United States Patent
Liu et al.

(10) Patent No.: US 8,753,893 B2
(45) Date of Patent: Jun. 17, 2014

(54) MULTI-DIMENSIONAL FLUID SENSORS AND RELATED DETECTORS AND METHODS

(75) Inventors: Ben H. Liu, Raleigh, NC (US); Jeffrey R. Soohoo, Raleigh, NC (US); Meghan E. Vidt, Winston-Salem, NC (US)

(73) Assignee: Ben H. Liu, Raleigh, NC (US)

( * ) Notice: Subject to any disclaimer, the term of this patent is extended or adjusted under 35 U.S.C. 154(b) by 443 days.

(21) Appl. No.: 12/994,302

(22) PCT Filed: Jun. 12, 2009

(86) PCT No.: PCT/US2009/003550
§ 371 (c)(1),
(2), (4) Date: Nov. 23, 2010

(87) PCT Pub. No.: WO2009/154710
PCT Pub. Date: Dec. 23, 2009

(65) Prior Publication Data
US 2011/0076783 A1    Mar. 31, 2011

Related U.S. Application Data

(60) Provisional application No. 61/073,865, filed on Jun. 19, 2008.

(51) Int. Cl.
*G01N 25/18* (2006.01)
*G01N 27/00* (2006.01)

(52) U.S. Cl.
USPC ........... 436/149; 436/518; 436/524; 436/525; 436/526; 435/7.1; 435/283.1; 435/287.1; 435/287.2; 422/50; 422/68.1; 422/82.01

(58) Field of Classification Search
USPC ........... 436/518, 524, 525, 526, 149; 435/7.1, 435/283.1, 287.1, 287.2; 422/50, 68.1, 422/82.01
See application file for complete search history.

(56) References Cited

U.S. PATENT DOCUMENTS

| | | | |
|---|---|---|---|
| 4,865,717 A | | 9/1989 | Setter et al. |
| 6,419,807 B1 | | 7/2002 | Davies et al. |
| 6,924,107 B2 | | 8/2005 | Liu |
| 2003/0159932 A1 | | 8/2003 | Betts et al. |
| 2004/0022677 A1 | * | 2/2004 | Wohlstadter et al. ........... 422/52 |
| 2008/0029391 A1 | * | 2/2008 | Mao et al. ................ 204/403.06 |
| 2009/0270274 A1 | | 10/2009 | Liu et al. |

OTHER PUBLICATIONS

International Search Report and Written Opinion for corresponding PCT application No. PCT/US2009/003550, mail date Feb. 10, 2010.

* cited by examiner

*Primary Examiner* — Melanie Y Brown
(74) *Attorney, Agent, or Firm* — Myers Bigel Sibley & Sajovec, P.A.

(57) ABSTRACT

The present invention provides multi-dimensional sensors with fluidic flow channels for processing fluid samples.

25 Claims, 15 Drawing Sheets

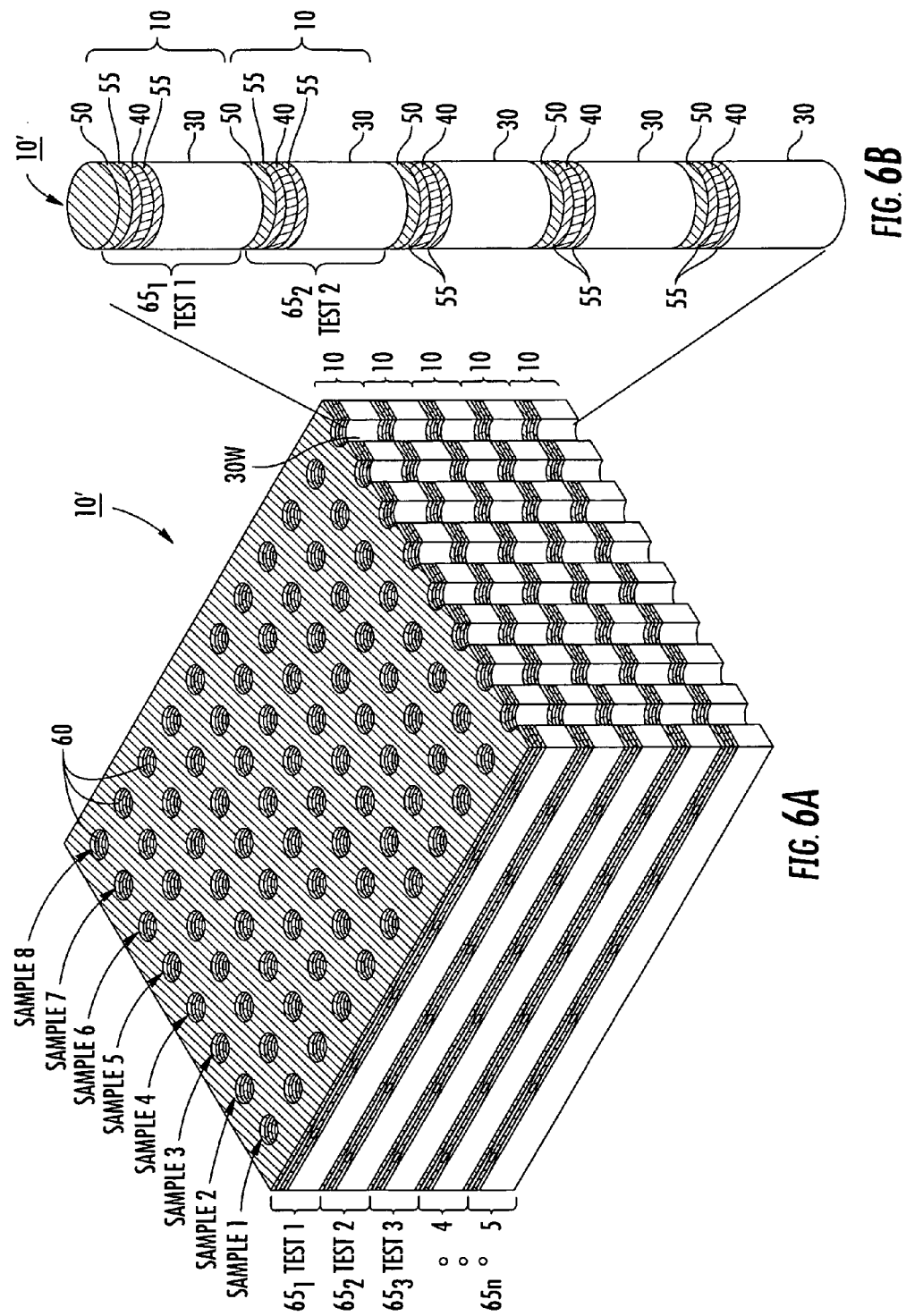

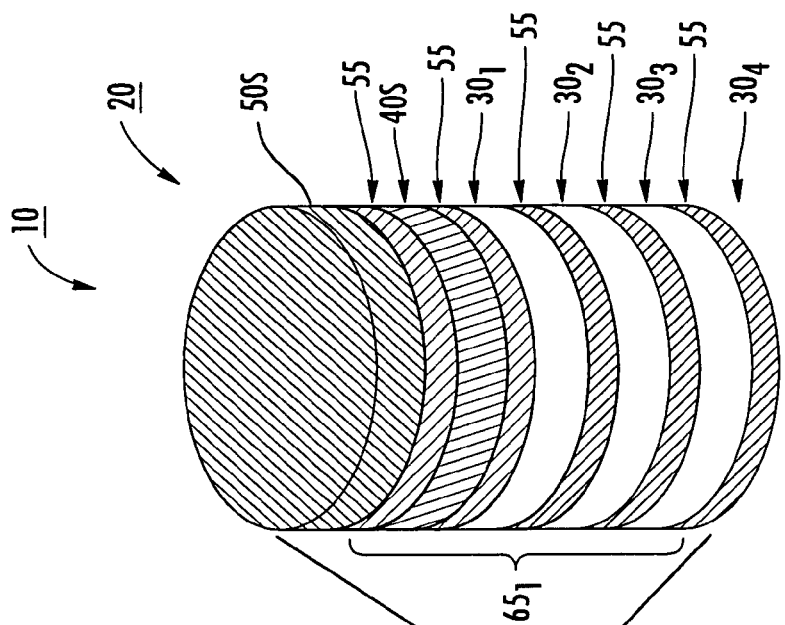
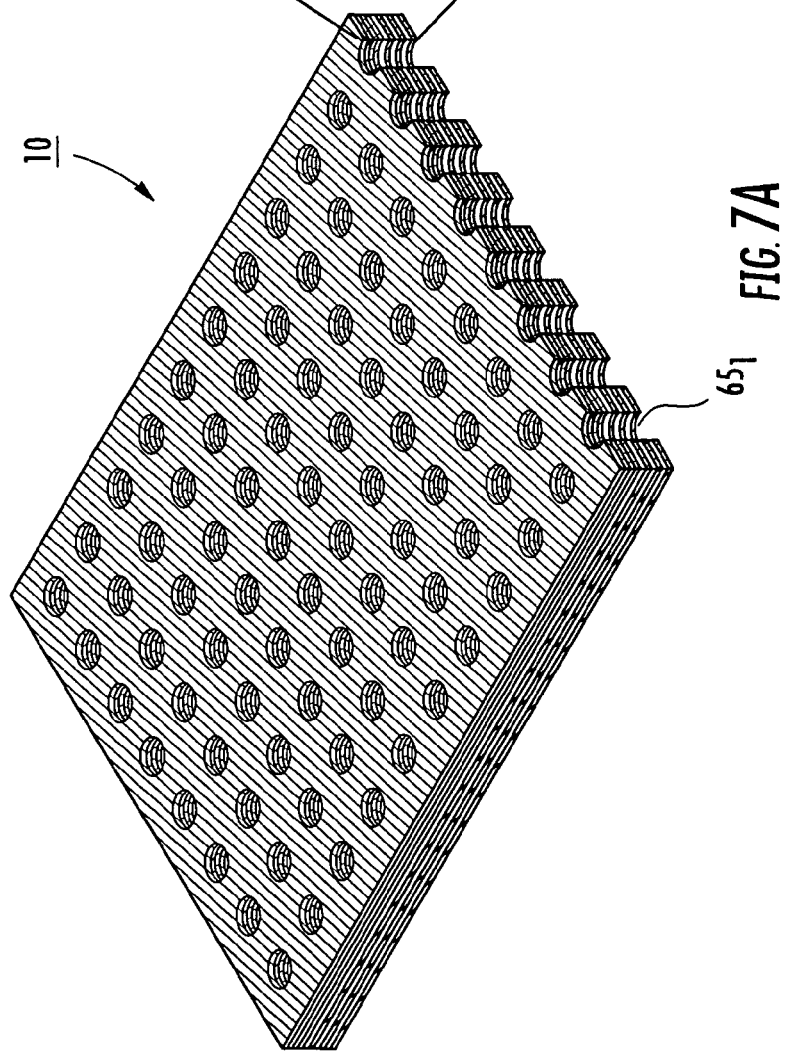

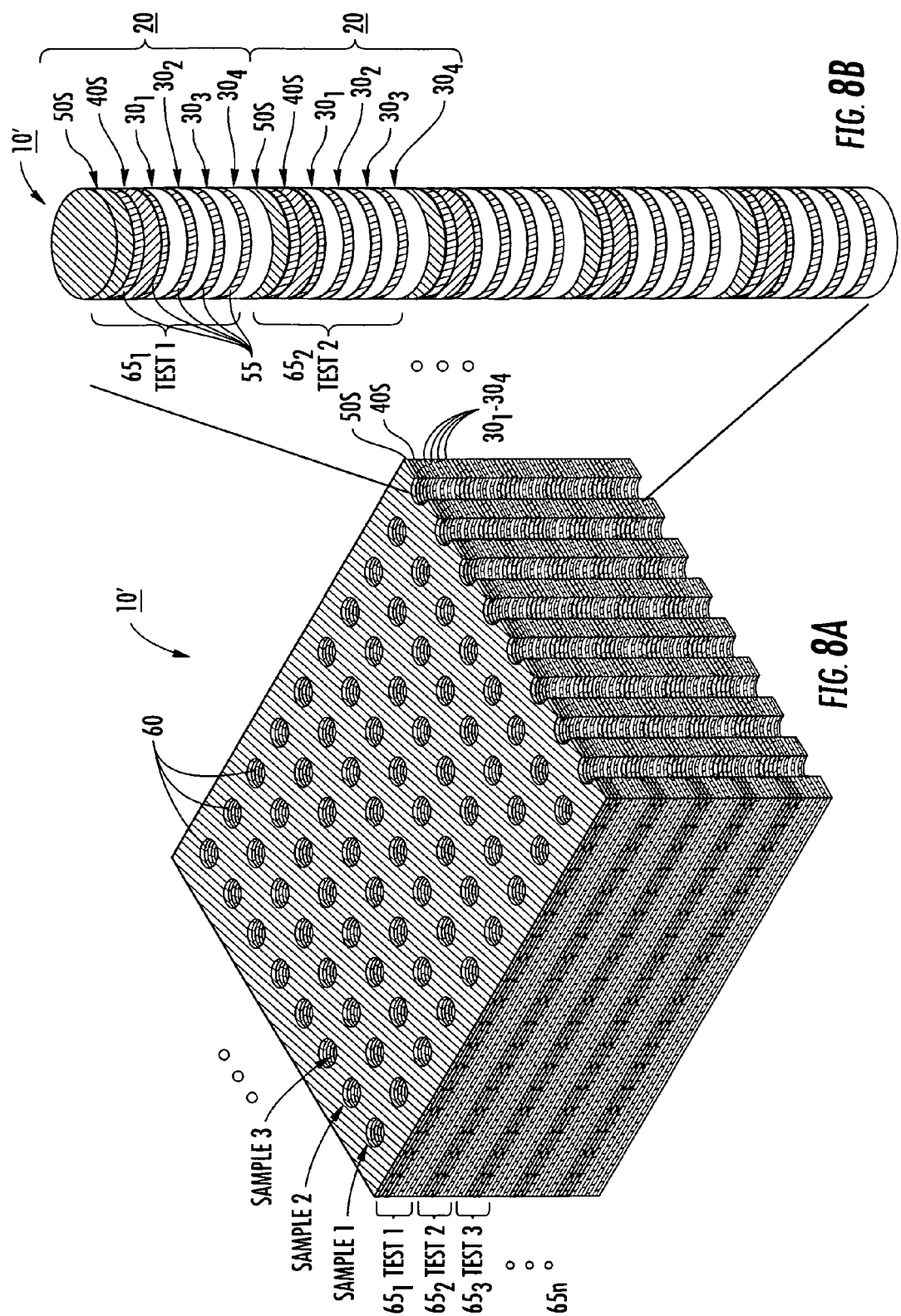

MULTI-DIMENSIONAL FLUID SENSORS AND RELATED DETECTORS AND METHODS

RELATED APPLICATIONS

This application is a 35 USC 371 national phase application of PCT/US2009/003550, filed Jun. 12, 2009, claims the benefit or priority of U.S. Provisional Application Ser. No. 61/073,865, filed Jun. 19, 2008, the contents of which are hereby incorporated by reference as if recited in full herein.

FIELD OF THE INVENTION

The present invention relates to sensors and automated analyzers thereof.

BACKGROUND

In the past, two-dimensional sensors, such as that shown in FIG. 1, have been used to analyze fluid samples. The two-dimensional sensors employ a flat platform with a counter electrode, reference electrode and working electrode. There remains a need to provide alternate sensor configurations, including, for example, those which can allow for one or more of: multiple sample analysis, multiple testing on a sample, and/or parallel sampling, as well as automated or semi-automated analysis instruments and system integration, for advancing low and high fluid sample throughput analysis, detection and/or diagnosis.

SUMMARY OF EMBODIMENTS OF THE INVENTION

Embodiments of the present invention are directed to multi-dimensional sensors, as well as one or more of detectors, analyzers and methods of generating, detecting and analyzing sensor data.

Some embodiments of the present invention are directed to multi-dimensional fluidic sensor devices. The sensor devices include a plurality of sensors. Each sensor has a set of associated electrodes, including at least one working electrode, a reference electrode and a counter electrode. Each electrode in the set of electrodes is positioned one above another (e.g., substantially vertically arranged or stacked) and isolated by an electrical insulator therebetween. Each set of electrodes has aligned apertures that define at least a part of a fluidic flow channel.

In particular embodiments, the working electrode has an inner wall that surrounds and defines the working electrode aperture, and at least a portion of the inner wall can optionally include a material selected to identify a target analyte in a sample flowing through a respective fluidic flow channel.

The target analyte may include a bioactive material of one or more of the following: an antibody, an antigen, a nucleic acid, a peptide nucleic acid, a ligand, a receptor, avidin, biotin, Protein A, Protein G, Protein L, a substrate for an enzyme and any combination thereof.

In some embodiments, the multi-dimensional sensor has a top surface and a bottom surface with a plurality of apertures arranged in columns and rows that form a plurality of fluidic flow channels. At least one set of the electrodes define at least a part of at least some of the plurality of fluidic flow channels.

The plurality of fluidic flow channels may be configured as a plurality of microfluidic flow channels.

Other embodiments are directed to three- or four-dimensional fluidic sensors. The sensor includes a sensor body having an array of fluidic flow channels formed therethrough. The fluidic flow channels include at least one sensor that has: (a) at least one working electrode having an upwardly extending inner wall surrounding an aperture; (b) at least one counter electrode having an upwardly extending inner wall surrounding an aperture and residing above or below the at least one working electrode; and (c) at least one reference electrode having an upwardly extending inner wall surrounding an aperture and residing above or below the at least one counter electrode. The working electrode aperture, the counter electrode aperture and the reference electrode aperture are aligned to define at least a portion of the fluidic flow channels.

The sensor can include an electrical insulator positioned between each of the electrodes.

In some embodiments, the sensor body comprises a plurality of stacked layers, including at least one working electrode layer, at least one reference electrode layer, and at least one counter electrode layer. Each layer has an array of apertures thereon configured and sized so that, when aligned, the array of apertures of each of the layers define at least a portion of the respective fluidic flow channels.

The layers can be sealed together, integral with each other, or snugly attached to define discrete fluid-tight fluidic flow channels.

Still other embodiments are directed to methods of monitoring fluid samples for detecting waterborne or airborne toxins or pathogens. The methods include: (a) providing a sensor body having a plurality of spaced apart fluidic flow channels, with the flow channels comprising at least one sensor having a set of vertically stacked electrodes with aligned apertures that define at least a portion of the fluidic flow channels; (b) flowing fluid samples through the fluidic flow channels; and (c) electronically detecting when a fluid sample tests positive for a selected analyte based on an output of the at least one sensor in a respective fluid channel.

The fluidic flow channels can optionally include a plurality of different sensors configured to detect different analytes. The flowing step can be carried out to serially flow a respective fluid sample through a plurality of different fluidic flow channels in the sensor body.

Yet other embodiments are directed to fluidic sensor devices. The devices include a sensor body having an array of microfluidic flow channels, the sensor body having a plurality of stacked layers, including at least one working electrode layer, at least one reference electrode layer, and at least one counter electrode layer. Each layer has a corresponding array of apertures thereon configured and sized so that, when aligned, the array of apertures of each of the layers defines at least a portion of the fluidic flow channels.

Yet other embodiments are directed to fluidic detector systems for analyzing fluid samples for target analytes. The detector systems include: (a) a sensor body having a plurality of fluid flow channels extending therethrough, the flow channels comprising a plurality of sensors, each sensor having at least one upwardly extending working electrode with an aperture, wherein the respective sensor working electrode is in communication with counter and reference electrodes, the sensors configured to detect different selected analytes in a fluid sample; and (b) a sensor detector in communication with the sensor body, the sensor detector configured to electronically poll each sensor in each flow channel individually to obtain a signal associated with a positive or negative test in response to the fluid sample passing through the fluidic flow channel.

Embodiments of this invention are directed to sensor bodies that can be assembled in a scalable configuration to include a selectable plurality of 3-D sensor arrays to form 4-D sensor arrays with between about 1-100,000 fluid channels, typically between about one and about 2000 fluid channels, depending on sensor size.

It is noted that features of embodiments of the invention as described herein may be methods, systems, computer programs or a combination of same although not specifically stated as such. The above and other embodiments will be described further below.

Further features, advantages and details of the present invention will be appreciated by those of ordinary skill in the art from a reading of the figures and the detailed description of the embodiments that follow, such description being merely illustrative of the present invention.

BRIEF DESCRIPTION OF THE DRAWINGS

FIG. 6A is an isometric view of a multi-test, multi-sample (4D) sensor array according to embodiments of the present invention.

FIG. 6B is an enlarged schematic view of the stacked relationship of the different layers and electrode groups shown in FIG. 6A.

FIG. 7A is an isometric view of a multi-test, multi-sample (4D) sensor array having a different electrode group arrangement according to embodiments of the present invention.

FIG. 7B is an exploded schematic illustration of the electrode arrangement shown in FIG. 7A.

FIG. 8A is an isometric view of a multi-test, multi-sample (4D) sensor array similar to that shown in FIG. 7A, but with additional groups of layers of the counter, reference and working electrodes according to embodiments of the present invention. FIG. 8B is an exploded schematic illustration of the electrode arrangement shown in FIG 8A.

DETAILED DESCRIPTION OF EMBODIMENTS OF THE INVENTION

Figure 1:
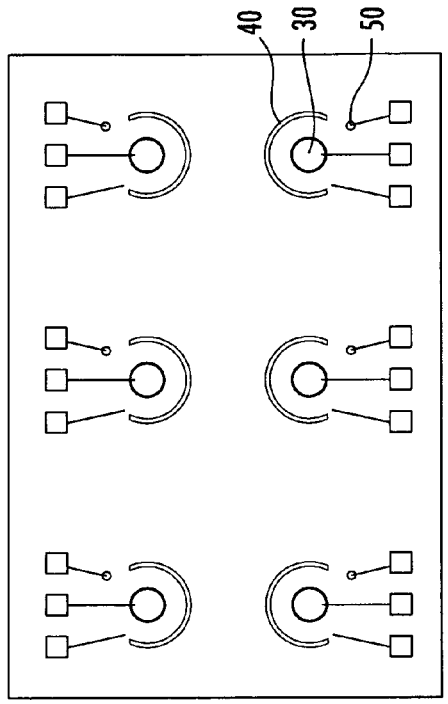
FIG. 1 is a schematic illustration of a conventional (prior art) two-dimensional sensor array.

The present invention is now described more fully hereinafter with reference to the accompanying drawings, in which embodiments of the invention are shown. This invention may, however, be embodied in many different forms and should not be construed as limited to the embodiments set forth herein; rather these embodiments are provided so that this disclosure will be thorough and complete and will fully convey the scope of the invention to those skilled in the art.

Like numbers refer to like elements throughout. In the figures, the thickness of certain lines, layers, components, elements or features may be exaggerated for clarity. Where used, broken lines illustrate optional features or operations unless specified otherwise.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising," when used in this specification, specify the presence of stated features, integers, steps, operations, elements components and/or groups or combinations thereof, but do not preclude the presence or addition of one or more other features, integers, steps, operations, elements, components and/or groups or combinations thereof.

As used herein, the term "and/or" includes any and all possible combinations or one or more of the associated listed items, as well as the lack of combinations when interpreted in the alternative ("or").

Also as used herein, phrases such as "between X and Y" and "between about X and Y" should be interpreted to include X and Y. Furthermore, phrases such as "between about X and Y" can mean "between about X and about Y." Also, phrases such as "from about X to Y" can mean "from about X to about Y."

Further, the term "about" as used herein when referring to a measurable value such as an amount or numerical value describing any sample, flow rate, composition or agent of this invention, as well as any dose, time, temperature, and the like, is meant to encompass variations of ±20% or lower, such as, for example, ±10%, ±5%, ±1%, ±0.5%, or even ±0.1% of the specified amount.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "connected" to, "coupled" with, "contacting," etc., another element, it can be directly on, attached to, connected to, coupled with and/or contacting the other element or intervening elements can also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature can include portions that overlap or underlie the adjacent feature.

Spatially relative terms, such as "under," "below," "lower," "over," "upper" and the like, may be used herein for ease of description to describe an element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus the exemplary term "under" can encompass both an orientation of over and under. The device may otherwise be oriented (rotated 90 degrees or at other orientations) and the spatially relative descriptors used herein interpreted accordingly. Similarly, the terms "upwardly," "downwardly," "vertical," "horizontal" and the like are used herein for the purpose of explanation only, unless specifically indicated otherwise.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section. Thus, a first element, component, region, layer or section discussed herein could be termed a second element, component, region, layer or section without departing from the teachings of the present invention. The sequence of operations (or steps) is not limited to the order presented in the claims or figures unless specifically indicated otherwise.

The term "sensor" refers to a device having one or more electrodes that can include analytical sites arranged on and/or in one or more substrates that permit one or more analyses to be performed on one or more fluid samples (e.g., microsamples) at the same time and/or at different times, typically, but not limited to, via flowable throughput through fluidic channels in the device. The fluid test sample can be in or comprise substantially gas or liquid. The test sample may include solid or particulate matter in the fluid. The flowable throughput may, in some embodiments, be high throughput conditions at a rapid flow rate(s). Flow speed can range from about 1 µl per minute for a simple flow-through assay (e.g., a sample passes through the fluid channel relatively slowly and no incubation is needed) to about 10 ml per minute (or more) for some tests or assays. The term "3D" or "three-dimensional" sensor or sensor array refers to a sensor with a stacked (one over another) electrode arrangement. The term "sensor array" means that the device has more than one sensor, typically arranged in a repeating or partially repeating pattern or layout on one or more surfaces. The term "4D" or "four-dimensional" sensor or sensor array refers to a sensor device that includes multiple sensors in a respective fluid channel that can carry out multiple tests per sample and/or analyze multiple samples, serially and/or in parallel. The multi-dimensional sensor arrays contemplated by embodiments of the present invention can be configured to concurrently accept and test multiple different samples and perform multiple different analyses on those samples and/or serially test a single sample or a plurality of samples.

A "fluidic flow channel" refers to a continuous or uninterrupted fluid pathway or channel typically extending through the sensor array, and typically with an opening at either an outside edge, an end or top or bottom of the sensor array (i.e., an inlet and an outlet) to allow the passage of fluid therethrough, from a sample entry location to a sample discharge location. The device can be configured to re-circulate or flow the fluid sample through one or more sensor channels over time, such as by using different fluid delivery systems, including, for example, pumps, vacuums or capillaries. A "microfluidic" flow channel is a miniaturized fluidic flow channel that accommodates a small fluid volume, typically between microliters and nanoliters of fluid. The microfluidic flow channel typically can hold or accommodate microscale amounts, e.g., microliters or less, such as, for example, 100 microliters or less, including nanoliters of fluid, which can be in the form of a gas or liquid as noted above. In some particular embodiments, each channel can, for example, hold from a sub-microliter volume (e.g., about 0.1 µl) to about a 100 µl volume. In some embodiments, for example, a channel can hold between about a 1 µl volume to about a 10 µl volume. For example, if one channel holds about 2 µl of liquid, a sensor with 20 channels can process about 40 µl of sample to test for 20 analytes.

Embodiments of the invention may be particularly suitable for lab or field testing of water systems, terrestrial or extraterritorial environments or fluids. For example, embodiments of the present invention may be used to monitor commodities or environments that may be subject to a security and/or health risk, e.g., air sampling, sampling of water systems including water treatment systems, and sampling of components or environments in food industries such as food production systems.

The sensor arrays of the present invention can be configured into any suitable geometric shape that defines the multiple sensor analysis sites. In some embodiments, the sensor arrays are configured as multi-layer cubes. The term "cube" is not limited to a "cube" shape, but is used broadly to refer to a box-like shape, such as a substantially rectangular shape or cube shape. However, the sensor arrays may have any desired geometric shape, and are not required to have a straight edge.

The term "bioactive" includes the term "bioreactive" and means an agent or material or composition that alone or when combined with another agent and exposed to a test sample will undergo a chemical or biological reaction and/or be altered in appearance or in another optically or electronically readable or detectable manner when a target analyte, e.g., constituent, antigen, antibody, bacterium, virus, ligand, protein contaminant, toxin, radioactive material and/or other material is present in the test sample. See, e.g., U.S. Pat. No.

6,294,107, the contents of which are hereby incorporated by reference as if recited in full herein.

The term "insulator" refers to a material that can provide electrical insulation between one or more adjacent components, e.g., between a counter and reference electrode and/or between a reference and working electrode. The insulator may also be able to provide fluid isolation between stacked layers. In other embodiments, two or more insulator layers may be used: at least one for electrical isolation and at least another one for fluid sealant. The fluid sealant material can cooperate with adjacent layers to define a substantially fluid-tight seal. The fluid sealant may be a thin gasket layer of any suitable material, such as, for example, a polymer, rubber, and/or metal. In some embodiments, the fluid sealant can be integrated into the electrical insulator and/or laminated and/or otherwise attached thereto. Where gaskets are used, the gasket may have a thickness that is substantially the same or more or less than an adjacent electrode layer, and is typically thinner than at least the working electrode layer. In some embodiments, the gasket can be formed of an elastically compressible material. In some embodiments, the fluid sealant can comprise a gasket of thermoplastic elastomers (including but not limited to Viton®, Buna-N, EPDM, and Versaflex® materials) and/or silicone rubbers.

Figure 2B:
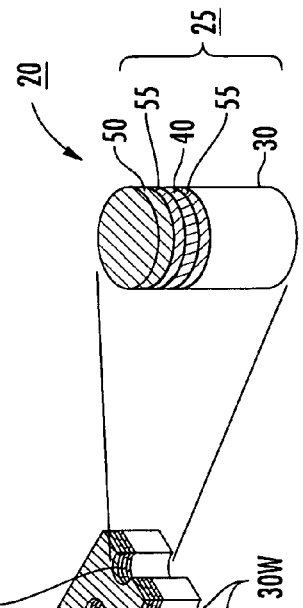
FIG. 2B is a greatly enlarged schematic view of a stacked electrode arrangement associated with the sensor shown in FIG. 2A according to embodiments of the present invention.
Figure 2A:
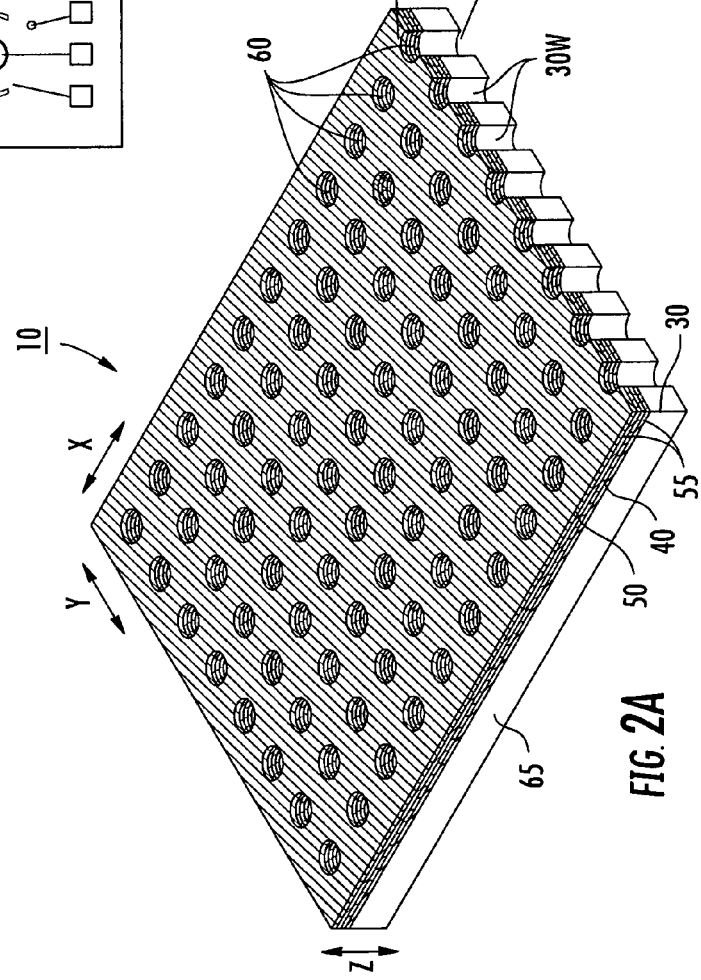
FIG. 2A is an isometric view of a multi-sample three or four dimensional sensor array according to embodiments of the present invention.

Turning now to the figures, FIG. 2A illustrates a sensor array 10 with each sensor 20 having an associated (typically substantially vertically-stacked) group of electrodes 25, including a working electrode 30, a reference electrode 40, and a counter electrode 50, one above another. As shown in FIG. 2B, an electrical insulator 55 can reside between the working electrode 30, the reference electrode 40, and the counter electrode 50. Although the sensor electrode groups 25 are shown in a tubular form in an exploded view such as in FIG. 2B (and FIG. 3, etc.), this shape is merely for ease of discussion. The sensor electrode groups 25 are configured with aligned apertures that define fluid flow channels 60 as shown in FIG. 2A.

Figure 3:
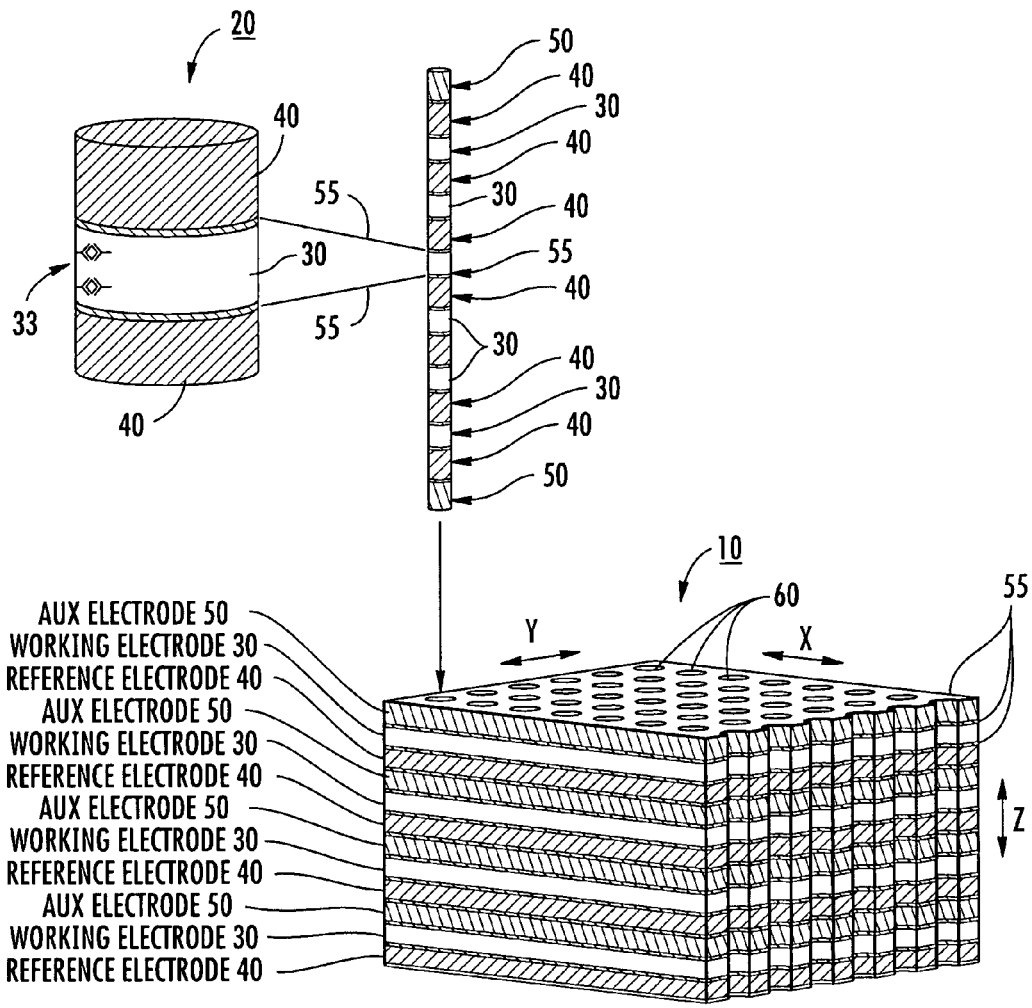
FIG. 3 is a schematic illustration of a stacked electrode relationship for a sensor array similar to that shown in FIGS. 2A and 2B illustrating insulating layers and reagents captured proximate a working electrode according to embodiments of the present invention.

FIG. 3 illustrates a different arrangement of the electrode group 25 and also illustrates that the working electrode 30 includes a coating 33 or is embedded or otherwise provided with a material that provides the desired test analyte for a respective sensor 20 for the test detection and/or monitoring. The coating 33 can comprise any suitable material such as, for example, capture reagents or any suitable bioreactive material.

FIG. 3 also illustrates that the insulator 55 both electrically insulates and provides a fluid seal between the adjacent layers, at least upon assembly. That is, the entire stacked configuration can be compressed together and the insulator 55 defines the fluid seal. Alternately, the fluid seal can exist upon assembly of the adjacent layers, such as by size and configuration or attachment means, including adhesive, brazing, welding and the like. Examples of suitable insulator materials include, for example, silicone rubber and certain thermo elastomers such as, for example, Versaflex®, and can, in some embodiments, have thicknesses ranging from between about 0.05 mm to about 10.0 mm. Different insulator materials can be used for different layers (or even partial layers).

FIGS. 2A and 3 illustrate that the sensor array 10 can include an array of fluid flow channels 60, having from n=1 to n=Y columns and from n=1 to n=X rows. Similarly, the flow channels can have from n=3 primary layers to n=Z layers to scale the sensor array in any desired configuration for the desired application. Each channel 60 may define a separate test path which can expose the test sample to a plurality of different test sites 20 at different levels of the working electrodes 30 in the flow channel 60.

In some embodiments, each electrode group 25 can define a discrete sensor 20 performing a different test, or the same test for reliability, and/or redundancy. Each working electrode 30 can comprise a different material 33, the same material, or even a different concentration or formulation of the same material for sensitivity or specificity of concentration or the like. Hence, a sensor array 10 can carry out a number of different tests e.g., tests n=1, to n, where "n" is any number between 1 and 500,000, typically, less than 100,000, and in some embodiments between about two to about 3000. As shown in FIG. 2A, each channel 60 can perform one test and in FIG. 3, the lower figure of the sensor array 10 illustrates three tests (e.g., three working electrodes 30) while the schematic illustrates six tests (e.g., six working electrodes 30). Also, each channel 60 residing in fluid communication in an X-Y location (row and column) of the sensor array 10 can define a different sample flow channel, allowing for a relatively large number of test samples to pass through the sensor array 10 or for one sample to be tested in the different samples over time. Thus, for example, in FIG. 2A, the sensor array 10 has 10 rows, X=10, 8 columns, Y=8, and one sensor in each channel 60, Z=1, thus, there are 80 tests 65 available in this sensor array 10 and up to 80 samples can be accommodated by this sensor array 10. FIG. 6A illustrates tests $65_1$-$65_n$. The bottom of FIG. 3 illustrates an example of a 4-D sensor array 10, where Z=3 (3 working electrodes 30 in each channel 60), eight rows, X=8, and 6 columns, Y=6. This sensor array 10 can accommodate up to 48 samples and perform up to 144 different tests (8 rows, 6 column and 3 sites per column, 8×6×3). The sensor array 10' can be configured to carry out a number of tests in a respective channel 60, typically between 1-1000, more typically between 1-50, and the sensor array 10' can evaluate one or more samples, such as, for example, but not limited to, up to about 100,000 samples, typically up to about 2000 samples, for each of the different tests (each test can be carried out by a corresponding sensor 20). It is noted that each working group of electrodes 25 that defines a respective sensor 20 can be configured to share one or more reference electrodes 40 and may include one or more working electrodes 30.

Figure 4:
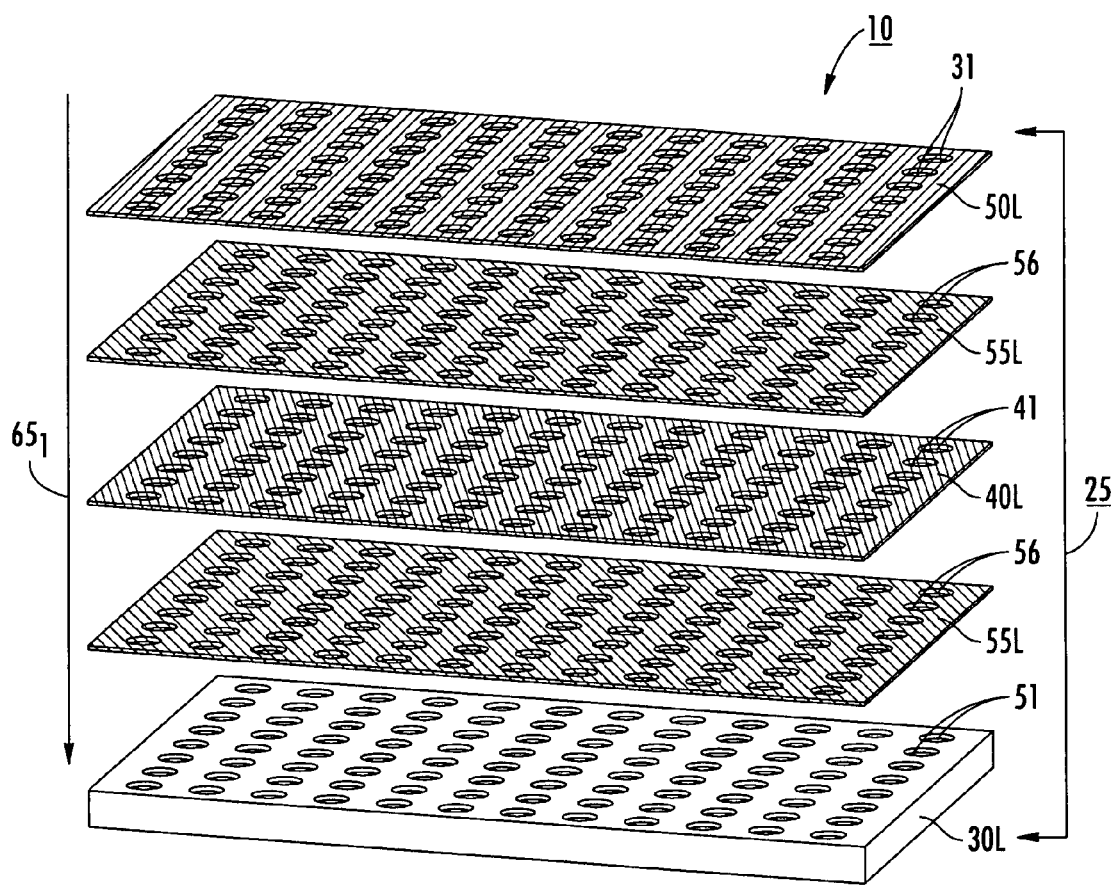
FIG. 4 is an isometric exploded view of a stacked counter, reference and working electrode configuration for a sensor according to embodiments of the present invention.

FIG. 4 is an exploded view of an exemplary 3-D sensor array 10. As shown, the sensor array 10 has a plurality of sensors 20 with each of the electrode groups 25 being defined by layers of adjacent materials that form the respective electrodes 30, 40, 50. The working electrode layer 30L, the reference electrode layer 40L and the counter electrode layer 50L are closely spaced and separated by a relatively thin insulation layers 55. Each of the layers 30L, 40L, 50L and 55L has corresponding patterns or arrays of apertures 31, 41, 51 and 56, that, when aligned and assembled, define the fluid channels 60. The layers 30L, 40L, 50L can be formed sequentially, one over the other, or may be laminated or otherwise held snugly together to define the fluidic flow channels 60. Thus, the layers may be integral with each other or separate or combinations of same. In particular embodiments, the working electrode layer 30 can have a thickness that is between about 0.05 mm to about 12 mm. The counter electrode 50 can comprise insert materials, such as noble metals or graphic carbon to avoid dissolution. Commonly used reference electrodes 40 include silver/silver-chloride electrodes, calomel electrodes, and hydrogen electrodes. The surface of a working electrode 30 is typically where the biochemical reactions take place. Besides behaving as an electrode for electroanalysis, the capture biomolecules, such as proteins, antibodies, antigens, or DNA probes, can be coated or otherwise disposed on the surface of the working electrode 30. The surface chemical properties of a working electrode 30 can vary depending on applications. For coating proteins on a working electrode 30, for example, the surface can be plated with a thin layer of gold.

Figure 15A:
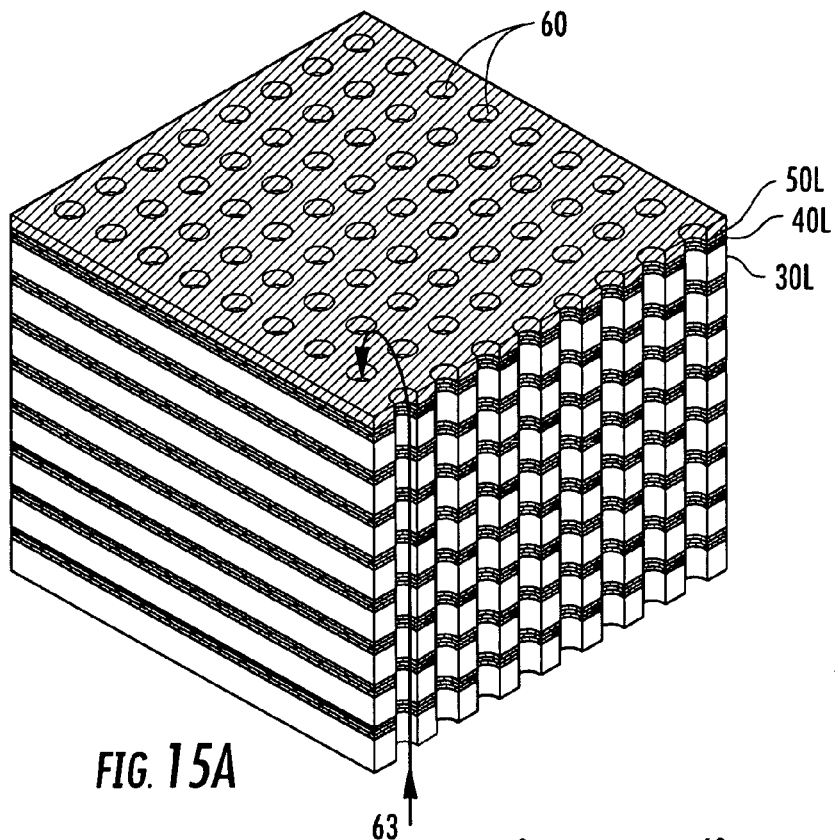
FIGS. 15A and 15B are isometric views of a multi-dimensional sensor configured to serially flow a sample through more than one fluid channel according to embodiments of the present invention.
Figure 15B:
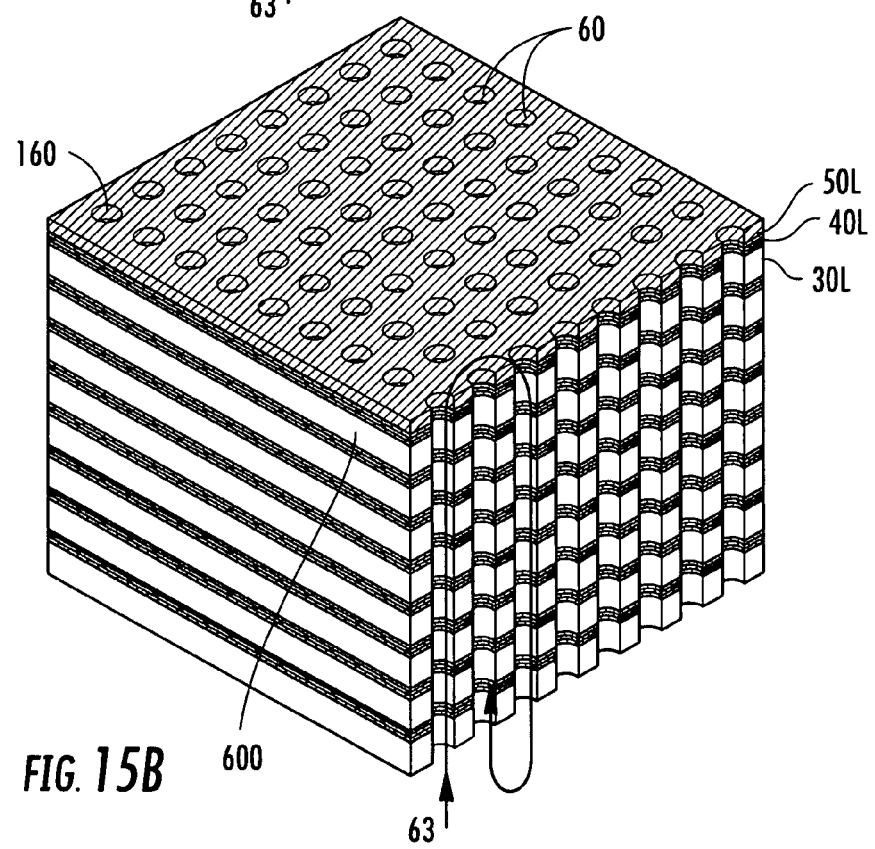

The working electrode layer 30 can comprise an analyte 33 for facilitating the testing and the sensor array 10 can define a single test $65_1$ for multiple samples, or multiple tests for one sample over time (by directing the sample 63 through another different channel 60 (serially) over time, such as shown by the arrows and fluid flow of sample 63 in FIGS. 15A, 15B). The analyte 33 can be placed on a wall or portion of a wall of each working electrode 30w forming a portion of the flow channel 60. The analyte 33 can be, for example, molded into or onto (e.g., alone or via a matrix), coated, sprayed, injected, poured, painted, covered, impregnated, vapor deposited, permeated, plated, soaked and/or embedded with an analyte or analytes 33. The material 33 can also be applied by a shrink-wrap or adhesively attachable strip or patch to or otherwise applied to an entire or partial wall of the working electrode 30. In some embodiments, each layer 30L has the same analyte 33. However, the invention is not limited thereto as different analytes 33 may be applied to different portions of the layer 30L.

In some embodiments, a first analyte such as a first bioactive agent or material can be present on a first portion of the wall 30w and a second analyte such as a second bioactive agent or material can be present on the same working electrode (not shown). In certain embodiments, the layer 30L can be immersed or soaked in a solution comprising the analyte 33, e.g., bioactive agent or material, resulting in the presence of the bioactive agent or material on both upper and lower (top and bottom) surfaces of the layer 30L, as well as on the wall surfaces 30W forming the apertures 31.

Figure 5:
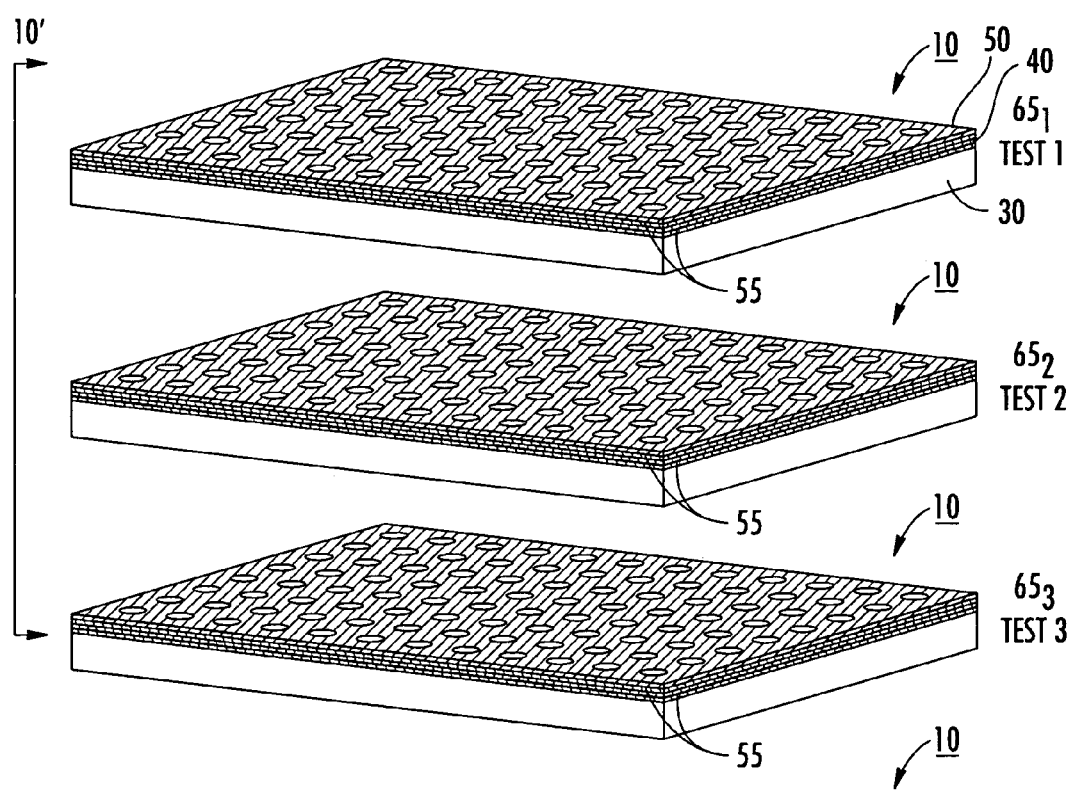
FIG. 5 is an isometric view of a sensor array illustrating that multiple sets of the counter, reference and working electrodes shown in FIG. 4 can be stacked to form a multi-test sensor according to embodiments of the present invention.

FIG. 5 illustrates that different selected 3-D sensor arrays 10 can be assembled together to form a 4-D sensor array 10'. In the embodiment, each 3-D sensor array 10 is shown as configured the same for ease of assembly. Also, in this embodiment, three sensor arrays 10 are stacked one above another to form three tests, $65_1, 65_2, 65_3$, that can be carried out on a test sample in a respective channel 60 substantially simultaneously. These sensor arrays 10 can be pre-assembled and provided to the lab or field test agency or may be selected onsite for a particular application. As such, the sensor arrays 10 can be supplied in kits of different sets of tests or ordered separately for subsequent assembly and use. Each three-dimensional sensor array 10 can have the same or a different material 33 for use in the four-dimensional sensor array 10'. Typically, once assembled, the sensors 10, 10' do not need to be disassembled to be analyzed or monitored as will be discussed further below.

FIGS. 6A and 6B illustrate a four-dimensional biosensor 10' with the multiple different 3-D sensors 10 assembled together to form $65_1$-$65_n$ (shown as 5 different) tests per sample. The exemplary sensor array 10' shown can accommodate up to 88 samples (if some channels 60 are not used to retest or re-circulate one or more samples).

FIGS. 7A and 7B illustrate that the sensor arrays 10 can be formed in different electrode layer configurations. As shown, each sensor 20' includes a plurality of working electrodes 30 with a shared counter electrode 50s and a shared reference electrode 40s. In some embodiments, an increased number of working electrodes 30 per sensor 20' (e.g., test $65_1$) with a potential decrease in their size may reduce electrical noise in one or more of the sensors 20'.

FIGS. 8A and 8B illustrate the sensor configuration 20' of FIGS. 7A and 7B in a 4-D sensor array 10'. Combinations of the sensor configurations 20' shown in FIGS. 7A and 7B as well as those shown in earlier or later figures may also be used as well as different numbers of working electrodes 30 and shared or dedicated reference and counter electrode configurations 40, 50, respectively.

Figures 9A, 9B:
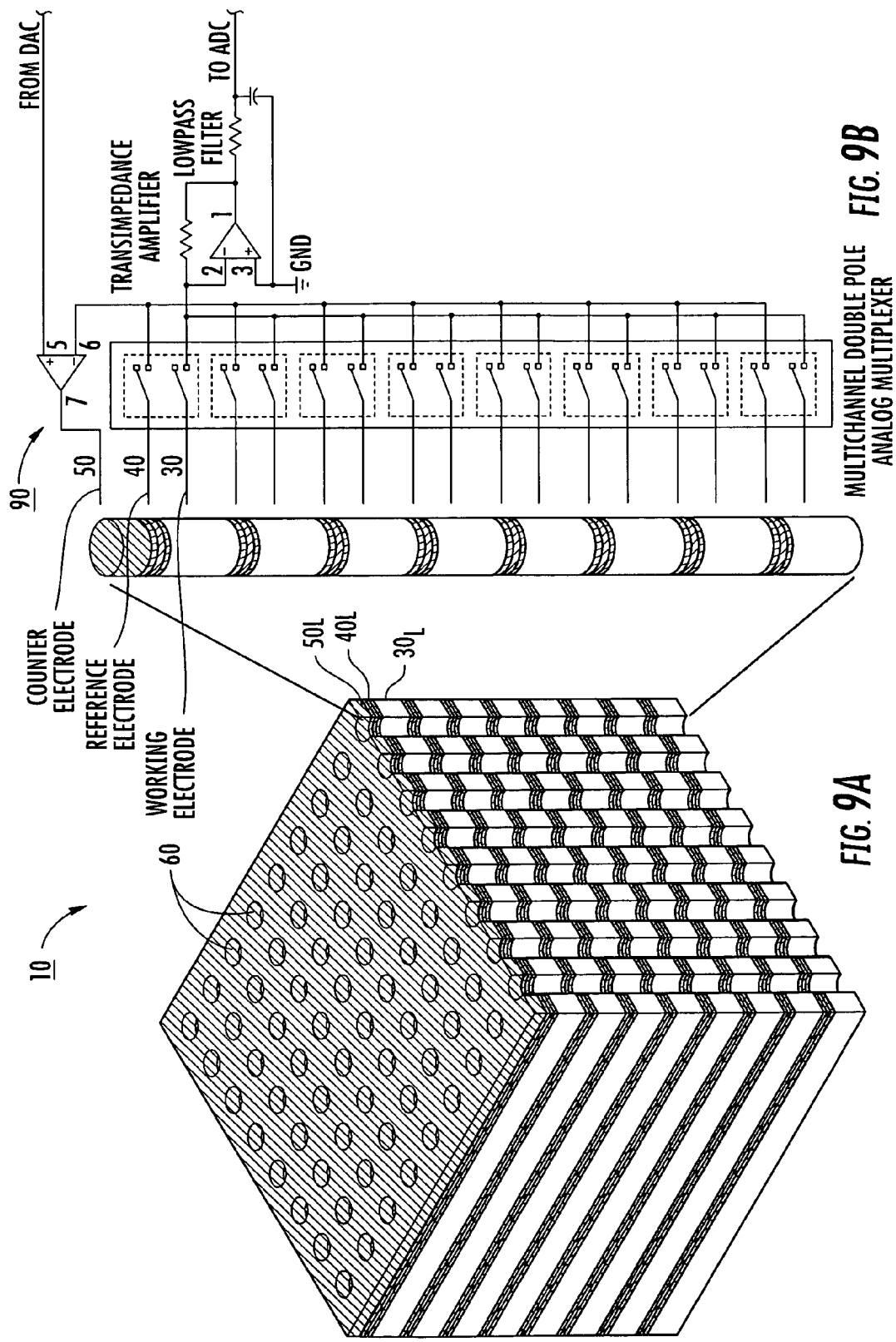
FIG. 9A is an isometric view of a multi-test, multi-sample (4D) sensor array with columns of discrete sensors according to embodiments of the present invention.
FIG. 9B is an exploded view of the electrode group configuration shown in the sensor array of FIG. 9A, illustrating associated electrical circuits that can be used to analyze the respective sensors in the sensor array according to embodiments of the present invention.

FIG. 9A illustrates an exemplary 4-D sensor array 10'. In this embodiment, the different sensors 20 share a counter electrode 50. FIG. 9B illustrates an exemplary circuit diagram of an interface circuit 90 with electronic connections to individual sensors 20. This circuit is modified where more than one counter electrode 50 is used as will be appreciated by one of skill in the art. The columns of sensors 20 defining respective channels 60 can be selected and switched electronically for activation, evaluation, monitoring detection and/or the like. In operation, the sensors 20 can be activated to become operational to carry out the fluid sampling. In other embodiments, the sensor 20 may be passive and only activated for detection or reading. The sensors 20 may be individually activated or a column or all of the sensors 20 may be concurrently or serially activated in a common flow channel 60. Each sensor 20 can be individually detected using a system detector that electronically communicates with the sensor electronics. Typically, the sensors 20 in a respective sample well/channel 60 are activated together. The sensors 20 can be read substantially with the activation or at a later time. Each sensor 20 in a channel 60 and/or in more than one channel 60 can be individually or serially read or monitored or read or monitored at the same time. Thus, the detection or monitoring of the sensors 20 can be done individually, serially and/or concurrently, allowing the sensors 20 to be polled in any desirable arrangement. In some embodiments, a review protocol can be used to "triage" the sensors 20 and identify those with increased strength of signal which can be read first.

The various electrode layers 30L, 40L, 50L can have electrical paths that extend to an outside perimeter of the sensor array 10, 10' to allow for each sensor to be (individually) activated and/or detected. The electrical paths in the various layers 30L, 40L, 50L be formed using vias or other paths (see, e.g., FIG. 9B).

Figure 10A:
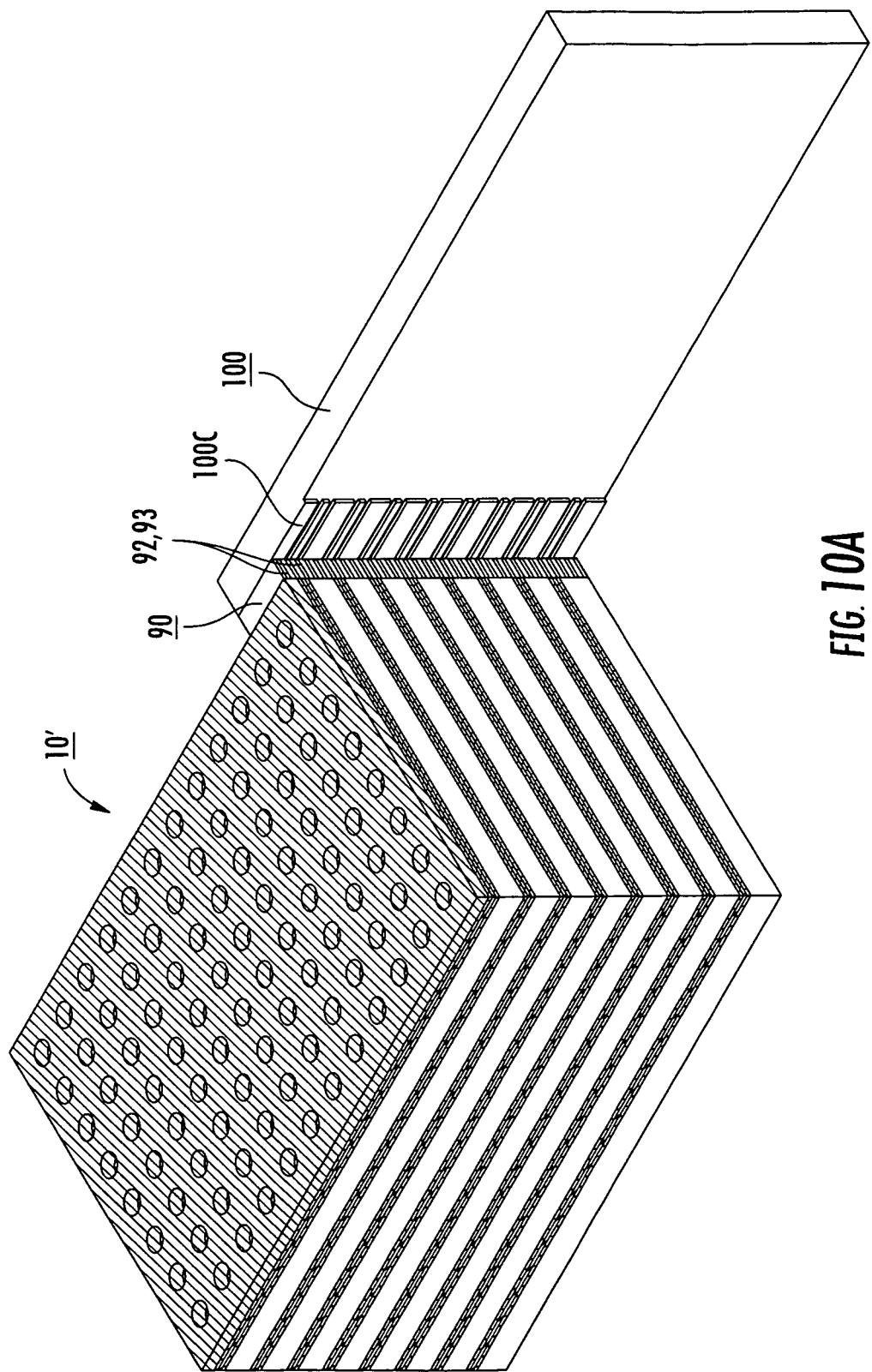
FIG. 10A is an isometric view of an electrical circuit interface that can be used to communicate with the sensors of the sensor array according to embodiments of the present invention.

FIG. 10A illustrates an electronic interface 100 that can provide the electrical circuit 90 to connect to the sensor array 10, 10' (shown as 10'). The interface 100 can include a polymer or other suitable case sandwiching alternating conductive/non-conductive layers 92, 93 extending between the sensor array 10' and the contacts on the interface (e.g., PCB) and in communication with the various electrode layers 30L, 40L, 50L associated with each sensor 20 in each channel 60.

Figure 10B:
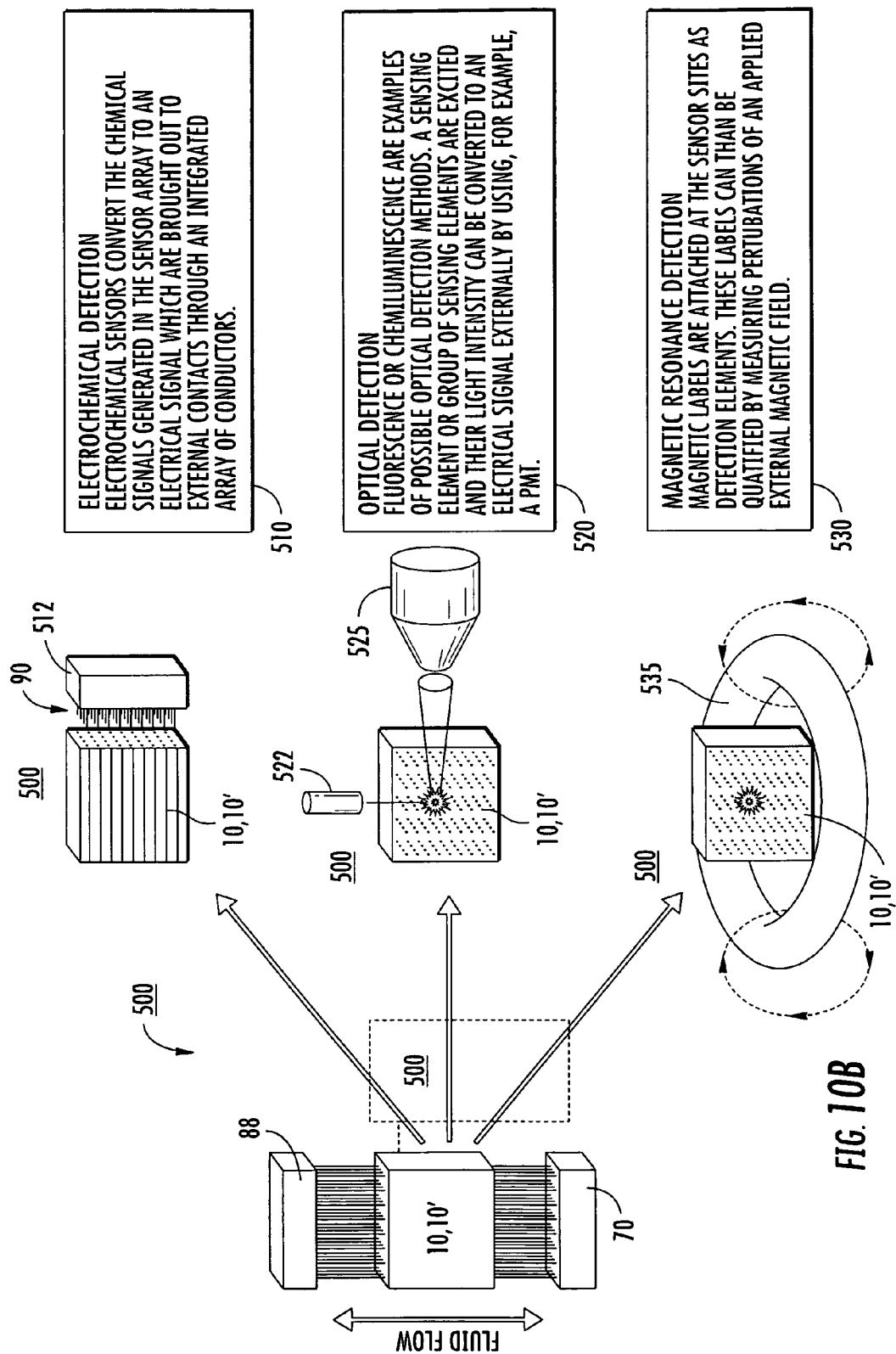
FIG. 10B is a schematic illustration of three exemplary detector systems that can be used to interface with and/or detect the sensor data of the sensor arrays according to embodiments of the present invention.

FIG. 10B schematically illustrates a sensor array 10, 10' in communication with fluid samples 70, and a fluid handling system 88 that can communicate with different exemplary sensor detectors 500 that can communicate with the sensor arrays 10, 10' and can extract test data therefrom. The fluidics assembly 88 can be configured to releasably hold sensor arrays 10, 10' of various heights; as such they may vary in use depending on the number of stacked 3-D sensor arrays 10' are used test-to-test or user-to-user (where the sensor arrays 10' are made from selectively attachable sensor arrays 10). As shown, in some embodiments, the fluidics assembly 88 resides in fluid communication with one or more of the flow channels 60 at an upper surface of the sensor array 10, 10'. Other fluid delivery/flow systems and configurations may also be used.

One exemplary detector 500 is an electrochemical detector 510. The electrochemical detector 510 reads electrochemical signals generated by the sensors 20 in the sensor array 10, 10'. The sensors 20 convert chemical signals to electrical signals and those signals are relayed or transmitted to external electrical contacts using an interface 90 with an array of conductors. The electrochemical detectors 510 can include de-multiplexers, amplifiers and A/D converters, filters and the like, as is known to those of skill in the art.

Another exemplary detector 500 is an optical detector 520 that comprises a light source, such as a laser 522, that can transmit a light into a sensor space to interrogate the sensors 20, and a light sensor 525 in communication with the sensor array 10, 10' and laser to be able to receive transmitted light in response thereto. In this embodiment, the sensors 20 are configured to optically change in opacity, color, intensity, transmissiveness, or the like, which can be optically detected. For example, sensors having fluorescent or chemiluminescent properties are examples of optical sensors. A sensing element or group of elements (e.g., working electrode 30) can be illuminated or excited and their light intensity can be converted to an electrical signal externally by using, for example, a PMT (photomultiplier tube). The detector 520 can include mirrors, lenses and other optical components suitable for optical detection as is known to those of skill in the art.

FIG. 10B also illustrates a third type of detector 500, a magnetic resonance detector 530. In this embodiment, magnetic labels can be attached to the sensor sites as detection probes or elements. These magnetic labels can be quantified or assessed by measuring perturbations of an applied external magnetic field 535 that extends proximate the sensor array 10, 10'.

Figure 11:
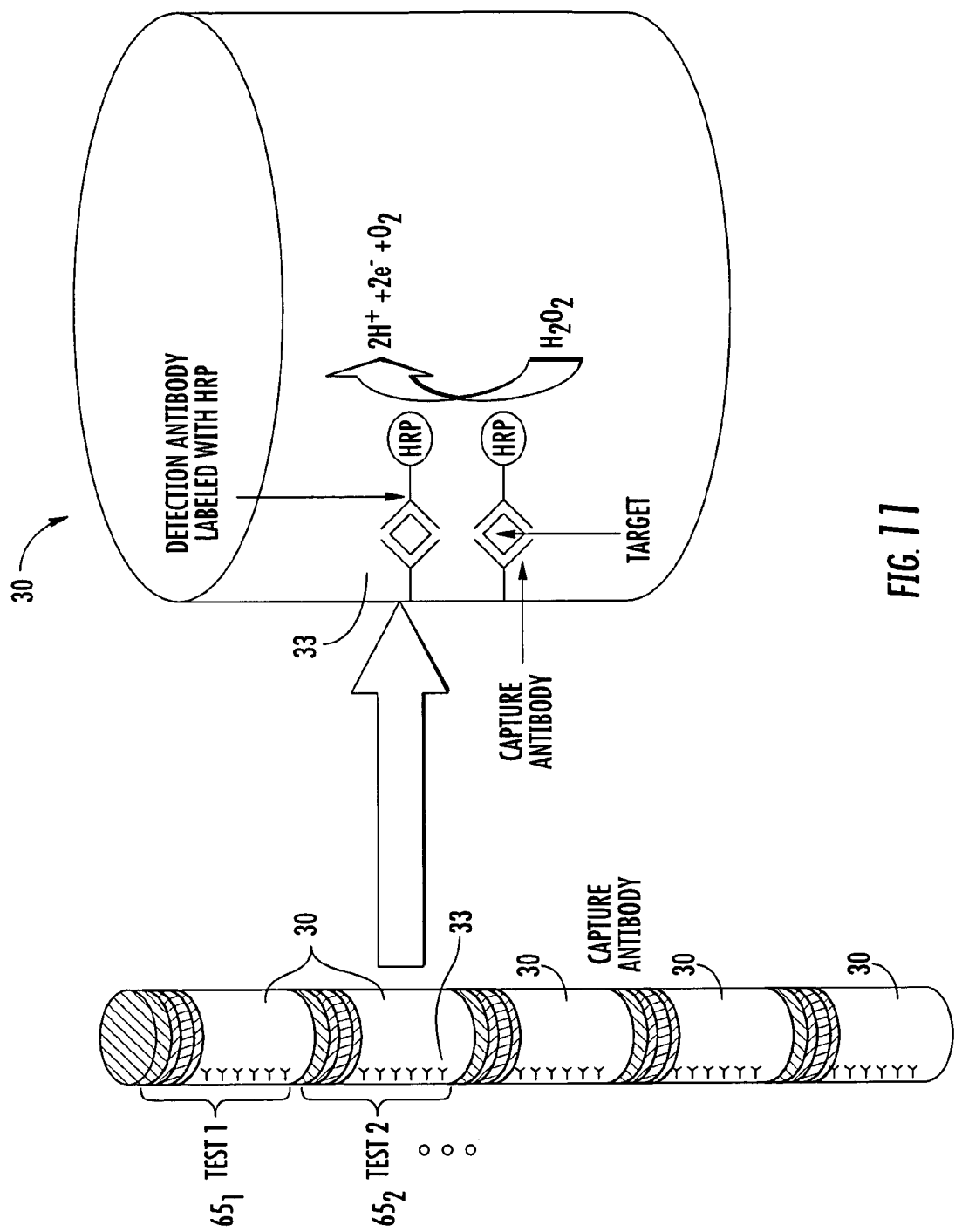
FIG. 11 is a schematic illustration of an example of a test operation using the stacked sensor array of embodiments of the present invention for an immunoassay to detect a target antigen according to embodiments of the present invention.
Figure 12:
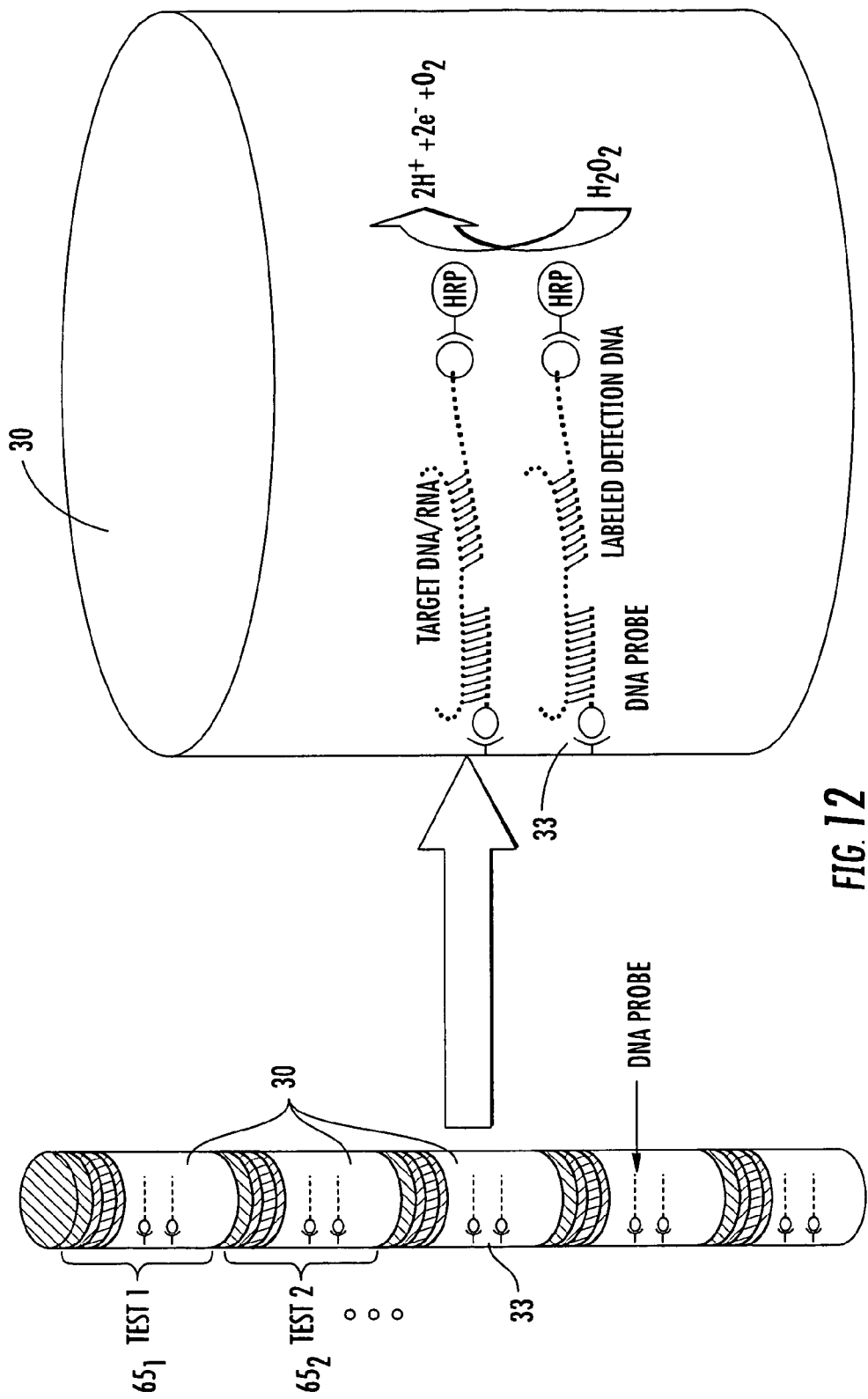
FIG. 12 is a schematic illustration of an example of a test operation using the stacked sensor array of embodiments of the present invention for a nucleic acid hybridization assay according to embodiments of the present invention.

FIGS. 11 and 12 illustrate exemplary test targets that can be analyzed according to particular embodiments of the present invention. As shown, FIG. 11 illustrates an immunoassay test with multiple test sites $65_1$-$65n$, and with the sensor 20, e.g., the working electrode 30 having an analyte 33 with a detection antibody with HRP. FIG. 12 illustrates an example of a DNA hybridization assay where the test material 33 on and/or in the sensor 20, e.g., working electrode 30 includes a target DNA probe.

Figure 13:
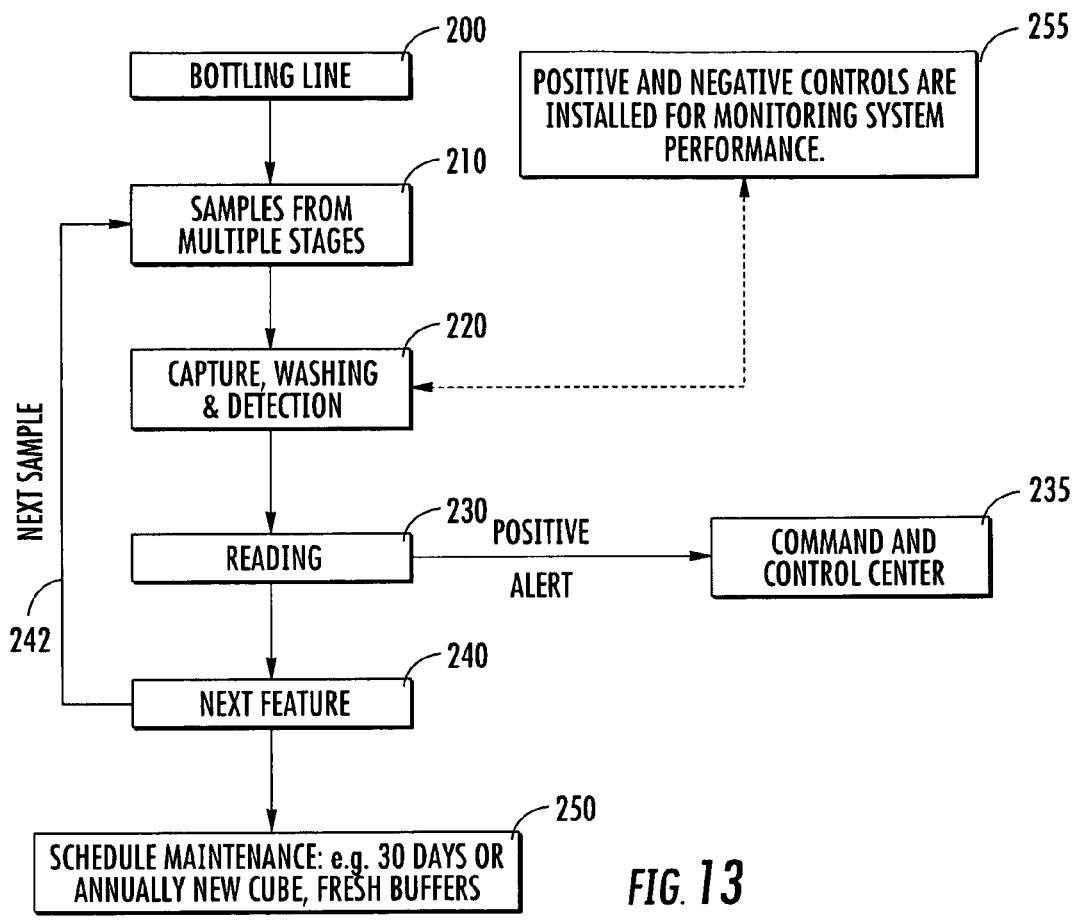
FIG. 13 is a flow chart of operations that can be carried out to detect fluid (typically liquid) food-borne pathogens according to embodiments of the present invention.

FIG. 13 is a flow chart of operations that can be used to carry out embodiments of the present invention. This flow chart is directed to monitoring for and/or detecting fluid borne pathogens in food or other consumer consumable items in a food production facility. At least one multi-dimensional sensor array 10, 10' can be placed in fluid communication with a production line (e.g., bottling or packaging stage in a production line) (block 200). One or more samples from different or multiple stages of the production line can be obtained (block 210). The samples can be captured, washed, filtered or processed (pre-processed) as appropriate, and flowed through one or more of the channels 60 in the sensor array 10, 10'. One or more sensors 20 in the array 10, 10', such as one or more in a flow channel 60, can be read (block 230) by a detector and an alert generated locally and/or to a command and control center (block 235) if a reading is positive. The command and control center can be in communication with a regulatory agency, such as, for example, the United States Food and Drug Administration or Homeland Security Office. Another sensor 20 in the array 10, 10', typically at a different level and/or testing for a different analyte, can be read (block 240). Another sample can be introduced into the sensor array 10, 10' (block 242). Maintenance of the sensor array 10, 10' can be scheduled for desired intervals, such as daily, weekly, monthly and the like (block 250). A new sensor array 10, 10' can be installed or the existing sensor array 10, 10' can be retrofitted with one or more components. The sensor arrays 10, 10' can be configured with modular components that allow for ease of repair/upgrade. Examples of refurbishment components include, for example, fresh buffers, insulators, fluid seals and the like. Both positive and negative controls can be installed in the sensor array 10, 10', or one array 10, 10' can include the positive controls and another the negative controls, for monitoring system performance assessment and reliability testing (block 255). For ease of assessment, a false positive control sensor may be adjacently positioned next to its "normal" sensor, although other placements in the sensor array 10, 10' or in a different sensor or sensor array are also possible.

Figure 14:
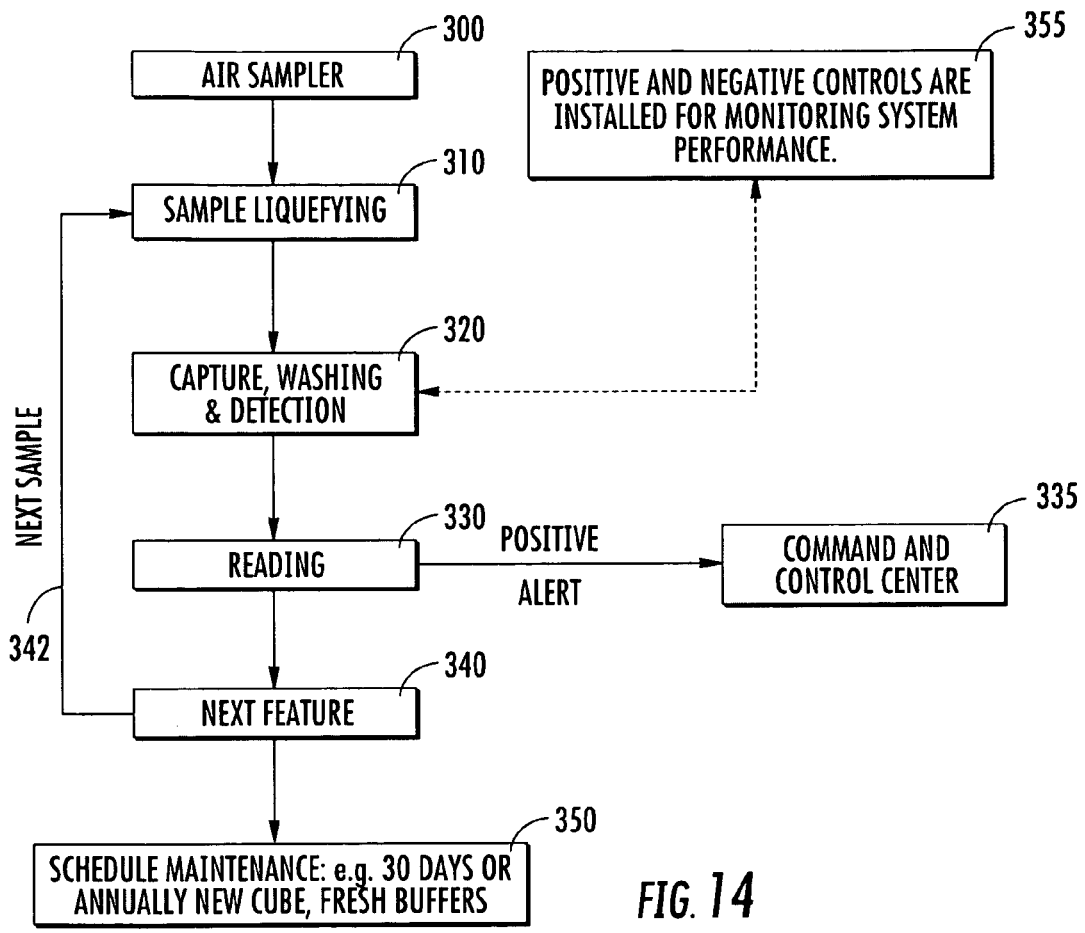
FIG. 14 is a flow chart of operations that can be carried out to detect airborne pathogens according to embodiments of the present invention.

FIG. 14 is a flow chart of operations that can be used to carry out embodiments of the present invention. This flow chart is directed to monitoring for and/or detecting airborne pathogens. An air sampler obtains samples of air (block 300). The air is introduced into the sensor array 10, 10' (block 320). The air may optionally be liquefied into a flowable sample prior to step 320 (block 310). At least one multi-dimensional sensor array 10, 10' can be placed in fluid communication with a production line (e.g., bottling or packaging stage in a production line) (block 200). The air samples can be captured, washed, filtered or processed (pre-processed) as appropriate, and flowed through one or more of the channels 60 in the sensor array 10, 10'. One or more sensors 20 in the array 10, 10', such as one or more in a flow channel 60, can be read (block 330) by a detector and an alert generated locally and/or transmitted to a command and control center (block 335) if a reading is positive. The command and control center can be in communication with a regulatory agency, such as, for example, the United States Food and Drug Administration or Homeland Security Office. Another sensor 20 in the array 10, 10', typically at a different level and/or testing for a different analyte, can be read (block 340). Another sample can be introduced into the sensor array 10, 10' (block 342) (after or with the first sample). Maintenance of the sensor array 10, 10' can be scheduled for desired intervals, such as daily, weekly, monthly and the like (block 350). A new sensor array 10, 10' can be installed or the existing sensor array 10, 10' can be retrofitted with one or more components. The sensor arrays 10, 10' can be configured with modular components that allow for ease of repair/upgrade. Examples of refurbishment components include, for example, fresh buffers, insulators, fluid seals and the like. Both positive and negative controls can be installed in the sensor array 10, 10' or one array 10, 10' can include the positive controls and another the negative controls, for monitoring system performance assessment and reliability testing (block 355). That is, to assess "false positives" or a control sensor may be used in communication with another sensor that is configured to render a regular positive report for a processed sample. For ease of assessment, a false positive control sensor may be adjacently positioned next to its "normal" sensor, although other placements in the sensor array 10, 10' or in a different sensor or sensor array are also possible.

FIGS. 15A and 15B illustrate that a single sample 63 can be routed through more than one channel 60. FIG. 15A illustrates that the sample travels from a bottom of a first channel 60 up through the top and back into the top of an adjacent or closely spaced channel 60. FIG. 15B illustrates that the sample 63 enters a first channel from the bottom, exits the top, and is rerouted to enter a bottom of another channel 60. In some embodiments, a single sample can be routed through each channel 60 of substantially the entire array 10, 10', or each channel in a row or a column of the array. The fluid delivery system (e.g., manifold) can be connected to take a discharged sample and reroute it into another channel 60. The sample entry for a respective channel 60 can be all from the top, all from the bottom or alternately from the top to the bottom, then bottom to top.

The sensor arrays 10, 10' can have a surface comprising predetermined electronically and/or optically readable indicia 600 as shown in FIG. 15B. Such indicia 600 can be placed on or in the sensor array 10, 10' during manufacture, or such indicia 600 can be placed after manufacture in the form of bar code, color code, symbols, watermark, icons, and/or a microchip with a secure "electronic handshake" or interface that communicates with an automated reader or analyzer. The location of the indicia 600 may be such that it is not readily visually apparent by the naked eye, and may be varied sensor to sensor 10, 10'. The location of the indicia 600 may be electronically correlated via a batch or manufacturer code or the like. The indicia 600 can be in any form or in multiple forms for redundancy, e.g., a bar code, a sticker, plate, notch, etching, etc. These indicia 600 can be used, for example, to identify the sensor array 10, 10' and/or other characteristics of the tests thereon (e.g., order or position of each sensor 20 in the stack, identification of bioactive agent(s) or material(s) present on the working electrode, status of testing of samples and/or analyzing of signal, etc.) and/or to verify the authenticity of the sensor array 10, 10'. These indicia 600 can be placed in any location (e.g., top, bottom, edge, under a gasket, on a gasket, or on a test surface 30w) and can also be present at multiple locations on the same array 10, 10'.

The indicia 600 can be visually, optically and/or electronically readable at the initiation of a test and/or before assembly of the sensors 10 to verify the type of test thereon and/or the authenticity of the chip to help control counterfeit products and/or inaccurate testing. For example, the electronic detector or reader 500 (see, e.g., FIG. 10B) can interrogate the sensor arrays 10, 10' and identify whether the sensor array is authorized or authentic. The reader can also be configured to alert a user when an unauthorized sensor array is detected and may even be programmed to block an analysis of such a sensor or prominently disclaim the test results where such authenticity is questioned. This may allow a clinician or laboratory technician or other user to retest a sample or investigate the test results rather than rely on potentially false test analysis.

Further embodiments of this invention include an automated method of analyzing multiple samples exposed to multiple analytical sites in a biosensor array, comprising: a) introducing a multiplicity of fluid samples into a fluid delivery system of an automated bioanalyzer; and b) flowing the multiplicity of fluid samples through the biosensor array having sets of electrodes defining at least one sensor with apertures defining microfluidic flow channels. An inner wall of at least one electrode in fluid communication with at least one of the flow channels. The electrode wall can include at least one bioactive agent or material that contacts a sample flowing thereover. An analyzer can analyze signals obtained from the sensors.

Non-limiting examples of a bioactive agent or material of this invention include an antibody, an antigen, a nucleic acid, a peptide nucleic acid, a ligand, a receptor, avidin, streptavidin, biotin, Protein A, Protein G, Protein L, a substrate for an enzyme, an anti-antibody, a toxin, a peptide, an oligonucleotide and any combination thereof.

The bioactive agent or material can be attached directly to the sensor, e.g., an inner wall of the working electrode and/or the bioactive agent or material can be attached indirectly (i.e., via a linker such as PEG (polyethylene glycol), EDC (N-3-Dimethylaminopropyl-N'-ethylcarbodiimide hydrochloride), glutaraldehyde, etc.). The bioactive agent can also be attached through a mediate layer of biotin, avidin, polylysine, BSA (bovine serum albumin), etc. as is known in the art. The bioactive agent or material of this invention can also be provided to an analytical site in a fluid solution, e.g., in order to detect a reaction at the analytical site.

In some embodiments, the bioactive material can be an antibody or antibody fragment and a signal is detected if an antigen/antibody complex is formed. In such embodiments, as an example, a first antibody or antibody fragment can be attached directly or indirectly to a wall or surface of the sensor via any variety of attachment protocols standard in the art. Then a fluid test sample is passed through a microfluidic flow channel such that the sample contacts an analytical site that comprises the immobilized first antibody or antibody fragment. If there is an antigen in the test sample that is specific for the immobilized first antibody or antibody fragment, the antigen will be bound (i.e., "captured") by the immobilized first antibody or antibody fragment, resulting in the formation of an antigen/antibody complex immobilized on the sensor. A fluid comprising a second antibody or antibody fragment that is detectably labeled is then passed through the microfluidic flow channel. The detectably labeled second antibody or antibody fragment is also specific for the antigen bound by the first immobilized antibody and will therefore bind to the captured antigen, thereby immobilizing the detectably labeled second antibody or antibody fragment at the analytical site. Upon subsequent analysis, the immobilized detectably labeled second antibody is detected at the analytical site according to the methods described herein and as are well known in the art for such detection. The result of the analytical testing is that the test sample comprises (e.g., is positive for) the target antigen.

In some embodiments, the bioactive material can be an antigen and a signal is detected if an antigen/antibody complex is formed. In such embodiments, as an example, an antigen (e.g., a peptide, polypeptide, amino acid sequence defining an epitope, etc.) is attached directly or indirectly to a surface of the sensor(s) via any variety of attachment protocols standard in the art. Then a fluid test sample is passed through a microfluidic flow channel such that the sample contacts an analytical site that comprises the immobilized antigen. If there is an antibody in the test sample that is specific for the immobilized antigen, the antibody in the sample will be bound (i.e., "captured") by the immobilized antigen, resulting in formation of an antigen/antibody complex immobilized on the sensor (e.g., working electrode wall). A fluid comprising a detectably labeled anti-antibody or antibody fragment specific for an antibody of the species from which the test sample was obtained is then passed through the microfluidic flow channel. The detectably labeled antibody or antibody fragment will bind the immobilized antibody captured by the antigen, thereby immobilizing the detectably labeled antibody or antibody fragment at the analytical site. Upon analysis, the immobilized detectably labeled antibody is detected at the analytical site according to the methods described herein and as are well known in the art for such detection. The result of the analytical testing is that the test sample comprises (e.g., is positive for) the target antibody.

In other embodiments, the bioactive material can be a nucleic acid or peptide nucleic acid and a signal is detected if a nucleic acid hybridization complex is formed. In such embodiments, as an example, a nucleic acid (e.g., an oligonucleotide) or peptide nucleic acid (PNA) is attached directly or indirectly to a surface of the sensor(s) via any variety of attachment protocols standard in the art. Then a fluid test sample is passed through a microfluidic flow channel such that the sample contacts an analytical site that comprises the immobilized nucleic acid or PNA. If there is a nucleic acid in the test sample that is complementary [either fully complementary or of sufficient partial complementarity to form a hybridization complex under the conditions of the assay (e.g., high stringency, medium stringency or low stringency as such terms are known in the art)], the nucleic acid in the sample will hybridize to (i.e., "be captured by") the immobilized nucleic acid or PNA, resulting in formation of a hybridization complex immobilized on the sensor. Upon (subsequent) analysis, the immobilized hybridization complex is detected at the analytical site according to the methods described herein and as are well known in the art for such detection. The result of the analytical testing is that the test sample comprises (e.g., is positive for) the target nucleic acid. In some embodiments, the immobilized hybridization complex can be detected because the nucleic acid in the test sample has been modified to comprise a detectable signal (e.g., fluorescence, chemiluminescence, radioactivity, electrochemical detection, enzymatic detection, magnetic detection, mass spectroscopy etc.).

The examples set forth above describing various assays that can be carried out in the sensors of this invention are not intended to be limiting in any way. If a target analyte can be captured by a corresponding bioactive agent that can be attached to the sensor, and the analyte can be detected by one of the detection methods listed above or other methods, then the assay can be performed using the sensors according to embodiments of this invention. The sensors can be employed to carry out any type of direct immunoassay, indirect immunoassay, competitive binding assay, neutralization assay, diagnostic assay, and/or biochemical assay. For example, a prenatal and/or neonatal TORCH assay, antigens and/or antibodies specific to toxoplasmosis, rubella, cytomegalovirus and herpes simplex virus can be attached on the sensors for capturing both IgG and IgM antibodies and/or viral antigens corresponding to the pathogens in human serum. As another example, antibodies and/or antigens specific to human Hepatitis B and C can be attached for detecting antibodies specific to surface and core antigens of the virus and/or the antigens in human serum samples. Another example, a substrate is immobilized on the sensor (e.g., inner wall of the working electrode) and a fluid sample is passed over the immobilized substrate to detect an enzyme that specifically acts on the immobilized substrate. A product of such enzyme activity can be detected, resulting in the identification of a test sample positive for the target enzyme.

Non-limiting examples of pathogens, agents of interest and/or contaminants that can be detected, identified and/or quantitated according to methods and devices of embodiments of the inventions include a majority of pathogens causing infectious diseases in human and animal, food and air borne pathogens, and pathogens which can be used as bioterrorism agents. The sensors can also be used to detect antibodies and proteins which can be used to diagnose a majority of infectious diseases and other diseases and conditions (e.g. thyroid function, pregnancy, cancers, cardiac disorders, autoimmune diseases, allergy, therapeutic drug monitoring, drug abuse tests, etc.). It would be well understood to one of ordinary skill in the art that the methods and sensors according to embodiments of this invention can also be employed to detect, identify and/or quantitate specific nucleic acids in a sample (e.g., mutations such as insertions, deletions, substitutions, rearrangements, etc., as well as allelic variants (e.g., single nucleotide polymorphisms). Nucleic acid based assays of embodiments of this invention can also be employed as diagnostics (e.g., to detect nucleic acid of a pathogen in a sample). In some embodiments, mutations of cytochrome P450 genes and blood clotting factor genes can be detected and/or identified. The sensors of embodiments of this invention can also be used to determine the level of a RNA transcript by hybridizing a labeled complex mixture of RNA samples onto surfaces coated with complementary strands of oligonucleotides or cDNAc.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

What is claimed is:

1. A multi-dimensional fluidic sensor device, comprising:
   a plurality of sensors, each sensor comprising a set of associated electrodes, including at least one working electrode, a reference electrode and a counter electrode, with each electrode in the electrode set positioned one above another and isolated by an electrical insulator therebetween, and wherein each set of electrodes has aligned apertures that extend through each of the electrodes to define at least a part of a fluidic flow channel.

2. A sensor according to claim 1, wherein the aligned apertures include a respective working electrode aperture, a reference electrode aperture and a counter electrode aperture, and wherein the working electrode has an inner wall that surrounds and defines the working electrode aperture, and wherein at least a portion of the inner wall comprises a predetermined material analyte for contacting a sample flowing through a respective fluidic flow channel.

3. A sensor according to claim 2, wherein the predetermined material comprises a bioactive material of one or more of the following: an antibody, an antigen, a nucleic acid, a peptide nucleic acid, a ligand, a receptor, avidin, biotin, Protein A, Protein G, Protein L, a substrate for an enzyme and any combination thereof.

4. A multi-dimensional fluidic sensor device, comprising:
   a plurality of sensors, each sensor comprising a set of associated electrodes, including at least one working electrode, a reference electrode and a counter electrode, with each electrode in the electrode set positioned one above another and isolated by an electrical insulator therebetween, and wherein each set of electrodes has aligned apertures that define at least a part of a fluidic flow channel,
   wherein the multi-dimensional sensor has a top surface and a bottom surface with a plurality of apertures arranged in columns and rows that form a plurality of fluidic flow channels, and wherein at least one set of the electrodes define at least a part of at least some of the plurality of fluidic flow channels.

5. A sensor according to claim 4, wherein the plurality of fluidic flow channels are microfluidic flow channels.

6. A sensor according to claim 4, wherein the fluidic flow channels comprise a plurality of sensors, each sensor comprising at least one working electrode, and wherein each working electrode resides in a respective fluid channel vertically spaced apart from another working electrode.

7. A sensor according to claim 6, wherein at least some of the sensors in at least one fluidic flow channel share a common reference and/or counter electrode.

8. A sensor according to claim 4, wherein the sensor is a 4-D sensor array comprising a plurality of sensors in each fluidic flow channel.

9. A sensor according to claim 8, wherein the 4-D sensor array is defined by a vertically stacked assembly of a plurality of 3-D sensor arrays, each of the 3-D sensor arrays having a single sensor in a respective fluidic flow channel, and wherein the plurality of 3-D sensors comprise at least one fluid seal that resides between adjacent pairs of 3-D sensors and seals the respective fluidic flow channels.

10. A multi-dimensional fluidic sensor device, comprising:
a plurality of sensors, each sensor comprising a set of associated electrodes, including at least one working electrode, a reference electrode and a counter electrode, with each electrode in the electrode set positioned one above another and isolated by an electrical insulator therebetween, and wherein each set of electrodes has aligned apertures that define at least a part of a fluidic flow channel,
wherein each sensor comprises a plurality of spaced apart working electrodes, one residing above another and separated by an electrical insulator.

11. A three-or four dimensional fluidic sensor, comprising:
a sensor body having an array of fluidic flow channels formed therethrough, wherein the fluidic flow channels comprise at least one sensor having:
at least one working electrode having an upwardly extending inner wall surrounding an aperture;
at least one counter electrode having an upwardly extending inner wall surrounding an aperture and residing above or below the at least one working electrode; and
at least one reference electrode having an upwardly extending inner wall surrounding an aperture and residing above or below the at least one counter electrode,
wherein the working electrode aperture, the counter electrode aperture and the reference electrode aperture are aligned to define at least a portion of the fluidic flow channels.

12. A fluidic sensor according to claim 11, further comprising an electrical insulator positioned between each of the electrodes.

13. A fluidic sensor according to claim 11, wherein the sensor body comprises a plurality of stacked layers, including at least one working electrode layer, at least one reference electrode layer, and at least one counter electrode layer, each layer having an array of apertures thereon configured and sized so that, when aligned, the array of apertures of each of the layers defines at least a portion of the respective fluidic flow channels.

14. A fluidic sensor according to claim 13, wherein the layers are sealed together, integral with each other or snugly attached to define discrete fluid-tight fluidic flow channels.

15. A fluidic sensor according to claim 11, wherein the sensor body comprises a plurality of sensors in each fluidic flow channel, each sensor having at least one working electrode that is vertically spaced apart above or below another working electrode of another sensor in a respective fluidic flow channel, and wherein the sensor comprises between about 50 to about 100,000 fluidic flow channels.

16. A fluidic sensor according to claim 15, wherein the respective sensors in a respective fluidic flow channel are configured to detect a different target analyte in a fluid sample flowing therethrough.

17. A fluidic sensor according to claim 11, wherein the working electrode comprises a material on or in the inner wall that causes the working electrode to produce a detectable electrical signal or change in an optical or magnetically detectable manner when a fluid having a predetermined substance therein is or has been in fluid communication with the inner wall of the working electrode in a respective fluidic flow channel.

18. A fluidic sensor according to claim 11, wherein each sensor comprises a plurality of vertically spaced apart working electrodes with respective apertures that define at least a portion of a respective fluidic flow channel.

19. A fluidic sensor according to claim 11, further comprising electrical traces that extend from each sensor to an outer perimeter of the sensor body for engaging an electrical interface circuit that can communicate with the working, reference and counter electrodes of each respective sensor.

20. A method of monitoring fluid samples for detecting waterborne or airborne toxins or pathogens, comprising:
providing a sensor device according to claim 1;
flowing fluid samples through fluidic flow channels comprising the sensors; and
electronically detecting when a fluid sample tests positive for a selected analyte based on an output of the at least one sensor in a respective fluidic flow channel.

21. A fluidic monitoring system according to claim 20, wherein the fluidic flow channels comprise a plurality of different sensors configured to test for different pathogens or toxins, and wherein the flowing step comprises serially flowing a respective fluid sample through a plurality of different fluidic flow channels in the sensor body.

22. A fluidic detector system for analyzing fluid samples for target substances or materials, comprising:
a sensor body having a plurality of fluid flow channels extending therethrough, the flow channels comprising a plurality of sensors, each sensor having at least one upwardly extending working electrode with a working electrode aperture, at least one counter electrode with a counter electrode aperture, and at least one reference electrode with a reference electrode aperture, wherein the apertures are aligned to define a portion of a respective fluid flow channel, and wherein at least one of the sensors is configured to test for a different selected analyte in a fluid sample relative to at least one other sensor; and
a sensor detector in communication with the sensor body, the sensor detector configured to electronically poll each sensor in each flow channel to obtain a signal associated with a positive or negative test in response to the fluid sample passing through the fluidic flow channel.

23. A system according to claim 22, wherein the sensor detector is configured to obtain a signal from a region of the sensor body that comprises predetermined authenticity or test data indicia.

24. A system according to claim 22, wherein the sensor body comprises sensors providing both positive and negative test controls.

25. A fluidic sensor device comprising:
a sensor body having an array of microfluidic flow channels, the sensor body having a plurality of layers residing one above another, including at least one working electrode layer, at least one reference electrode layer, and at least one counter electrode layer, wherein each layer has a corresponding array of apertures thereon sized and aligned so that the array of apertures of each of the layers define at least a portion of the fluidic flow channels.

* * * * *

UNITED STATES PATENT AND TRADEMARK OFFICE
CERTIFICATE OF CORRECTION

PATENT NO. : 8,753,893 B2
APPLICATION NO. : 12/994302
DATED : June 17, 2014
INVENTOR(S) : Liu et al.

Page 1 of 1

It is certified that error appears in the above-identified patent and that said Letters Patent is hereby corrected as shown below:

In the Specification:
Column 1, Related Applications, Line 7:
 Please correct "filed June 12, 2009, claims the"
  to read -- filed June 12, 2009, which claims the --

Signed and Sealed this
Sixth Day of January, 2015

Michelle K. Lee
*Deputy Director of the United States Patent and Trademark Office*